United States Patent [19]
Luster et al.

[11] Patent Number: 5,824,299
[45] Date of Patent: Oct. 20, 1998

[54] MODULATION OF ENDOTHELIAL CELL PROLIFERATION WITH IP-10

[75] Inventors: Andrew Luster, Wellesley; Philip Leder, Chestnut Hill, both of Mass.

[73] Assignee: President & Fellows of Harvard College, Cambridge, Mass.

[21] Appl. No.: 493,638

[22] Filed: Jun. 22, 1995

[51] Int. Cl.[6] .......................... A61K 38/19; A61K 38/16
[52] U.S. Cl. ................................ 424/85.1; 514/2
[58] Field of Search ................................ 514/2; 424/85.1

[56] References Cited

FOREIGN PATENT DOCUMENTS

WO 94/04670  3/1994  WIPO .

OTHER PUBLICATIONS

J. Folkman, "Angiogenesis in cancer, vascular, rheumatoid and other disease", Nature Medicine 1:27–31, 1995.

Luster et al., "γ–Interferon transcriptionally regulates an early–response gene containing homology to platelet proteins", Nature 315:672–675, 1985.

Gottlieb et al., "Detection of a γ Interferon–induced protein IP–10 in psoriatic plaques", J. Exp. Med. 168:941–948, 1988.

Smoller et al., "Fixed drug eruptions: evidence for a cytokine–mediated process", J. of Cutaneous Pathology 18(1):13–19, 1990.

Taub et al., "Recombinant Human Interferon–inducible protein 10 is a chemoattractant for human monocytes and T lymphocytes and promotes T cell adhesion to endothelial cells", J. Exp. Med. 177:1809–1814, 1993.

Sato et al., "Platelet factor 4 blocks the binding of basic fibroblast growth factor to the receptor and inhibits the spontaneous migration . . . ", Bioch. and Biophy. Res. Comm. 172:595–600, 1990.

Whitson et al., "Platelet factor 4 selectively inhibits binding of TGF–$\beta_1$ to the type 1 TGF–$\beta_1$ receptor", J. Cell. Bioch. 47:31–42, 1991.

Kaplan et al., "The expression of a γ Interferon–induced protein (IP–10) in delayed immune responses in human skin", J. Exp. Med. 166:1098–1108, 1987.

Primary Examiner—Stephen Walsh
Assistant Examiner—Daryl A. Basham
Attorney, Agent, or Firm—Clark & Elbing LLP

[57] ABSTRACT

Disclosed are methods for modulating endothelial cell proliferation. Also, disclosed are methods of detecting compounds which inhibit IP-10 and PF4 binding to a HSPG receptor.

13 Claims, 14 Drawing Sheets a CGGGAGACATTCCTCAATTGCTTAGACATATTCTGAGCCTACAGCAGAGGAACCTCCAGTCTCAGCACC 69

```
  1 Met Asn Gln Thr Ala Ile Leu Ile Cys Cys Leu Ile Phe Leu Thr Leu Ser Gly
    ATG AAT CAA ACT GCG ATT CTG ATT TGC TGC CTT ATC TTT CTG ACT CTA AGT GGC  123
                     ↓
 19 Ile Gln Gly Val Pro Leu Ser Arg Thr Val Arg Cys Thr Cys Ile Ser Ile Ser
    ATT CAA GGA GTA CCT CTC TCT AGA ACC GTA CGC TGT ACC TGC ATC AGC ATT AGT  177

37 Asn Gln Pro Val Asn Pro Arg Ser Leu Glu Lys Leu Glu Ile Ile Pro Ala Ser
    AAT CAA CCT GTT AAT CCA AGG TCT TTA GAA AAA CTT GAA ATT ATT CCT GCA AGC  231

55 Gln Phe Cys Pro Arg Val Glu Ile Ile Ala Thr Met Lys Lys Lys Gly Glu Lys
    CAA TTT TGT CCA CGT GTT GAG ATC ATT GCT ACA ATG AAA AAG AAG GGT GAG AAG  285

73 Arg Cys Leu Asn Pro Glu Ser Lys Ala Ile Lys Asn Leu Leu Lys Ala Val Ser
    AGA TGT CTG AAT CCA GAA TCG AAG GCC ATC AAG AAT TTA CTG AAA GCA GTT AGC  339
                                         98
 91 Lys Glu Met Ser Lys Arg Ser Pro
    AAG GAA ATG TCT AAA AGA TCT CCT TAAAACCAGAGGGGAGCAAAATCGATGCAGTGCTTCCAA  402
```

GGATGGACCACACAGAGGCTGCCTCTCCCATCACTTCCCTACATGGAGTATATGTCAAGCCATAATTGTTC 473

TTAGTTTGCAGTTACACTAAAAGGTGACCAATGATGGTCACCAAATCAGCTGCTACTACTCCTGTAGGAAG 544

GTTAATGTTCATCATCCTAAGCTATTCAGTAATAACTCTACCCTGGCACTATAATGTAAGCTCTACTGAGG 615

TGCTATGTTCTTAGTGGATGTTCTGACCCTGCTTCAAATATTTCCCTCACCTTTCCCATCTTCCAAGGGTA 686

CTAAGGAATCTTTCTGCTTTGGGGTTTATCAGAATTCTCAGAATCTCAAATAACTAAAAGGTATGCAATCA 757

AATCTGCTTTTTAAAGAATGCTCTTTACTTCATGGACTTCCACTGCCATCCTCCCAAGGGGCCCAAATTCT 828

TTCAGTGGCTACCTACATACAATTCCAAACACATACAGGAAGGTAGAAATATCTGAAAATGTATGTGTAAG 899

TATTCTTATTTAATGAAAGACTGTACAAAGTATAAGTCTTAGATGTATATATTTCCTATATTGTTTTCAGT 970

GTACATGGAATAACATGTAATTAAGTACTATGTATCAATGAGTAACAGGAAAATTTTAAAAATACAGATAG 1041

ATATATGCTCTGCATGTTACATAAGATAAATGTGCTGAATGGTTTTCAAATAAAAATGAGGTACTCTCCTG 1112

GAAATATTAAGAAAGACTATCTAAATGTTGAAGATCAAAGGTTAATAAAGTAATTATAACTAAAAAAAAAA 1183

AAAAAAAAAAAAAAA

Fig. 11

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

CGCAAGCTTC GGGAGACATT CCTCAATTGC                            30

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

CGCGGATCCA GGAGATCTTT TAGACATTTC                            30

( 2 ) INFORMATION FOR SEQ ID NO:3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

ACAGATCTAA GCGCTTCATC CACCGCTGA                             29

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GCGAGATCTA GGAGCCCTTT TAGACCTTTT                            30

( 2 ) INFORMATION FOR SEQ ID NO:5:

( i ) SEQUENCE CHARACTERISTICS:
        ( A ) LENGTH: 1185 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS ( B ) LOCATION: 80..374

( x i ) SEQUENCE DESCRIPTION: SEQ ID NO:5:

```
ACACATAATT CGGGAGACAT TCCTCAATTG CTTAGACATA TTCTGAGCCT ACAGCAGAGG          60

AACCTCCAGT CTCAGCACC ATG AAT CAA ACT GCG ATT CTG ATT TGC TGC CTT          112
                    Met Asn Gln Thr Ala Ile Leu Ile Cys Cys Leu
                     1               5                  10

ATC TTT CTG ACT CTA AGT GGC ATT CAA GGA GTA CCT CTC TCT AGA ACC           160
Ile Phe Leu Thr Leu Ser Gly Ile Gln Gly Val Pro Leu Ser Arg Thr
            15                  20                  25

GTA CGC TGT ACC TGC ATC AGC ATT AGT AAT CAA CCT GTT AAT CCA AGG           208
Val Arg Cys Thr Cys Ile Ser Ile Ser Asn Gln Pro Val Asn Pro Arg
        30                  35                  40

TCT TTA GAA AAA CTT GAA ATT ATT CCT GCA AGC CAA TTT TGT CCA CGT           256
Ser Leu Glu Lys Leu Glu Ile Ile Pro Ala Ser Gln Phe Cys Pro Arg
    45                  50                  55

GTT GAG ATC ATT GCT ACA ATG AAA AAG AAG GGT GAG AAG AGA TGT CTG           304
Val Glu Ile Ile Ala Thr Met Lys Lys Lys Gly Glu Lys Arg Cys Leu
 60                  65                  70                  75

AAT CCA GAA TCG AAG GCC ATC AAG AAT TTA CTG AAA GCA GTT AGC AAG           352
Asn Pro Glu Ser Lys Ala Ile Lys Asn Leu Leu Lys Ala Val Ser Lys
                80                  85                  90

GAA ATG TCT AAA AGA TCT CCT T AAAACCAGAG GGGAGCAAAA TCGATGCAGT            404
Glu Met Ser Lys Arg Ser Pro
                95

GCTTCCAAGG ATGGACCACA CAGAGGCTGC CTCTCCCATC ACTTCCCTAC ATGGAGTATA         464

TGTCAAGCCA TAATTGTTCT TAGTTTGCAG TTACACTAAA AGGTGACCAA TGATGGTCAC         524

CAAATCAGCT GCTACTACTC CTGTAGGAAG GTTAATGTTC ATCATCCTAA GCTATTCAGT         584

AATAACTCTA CCCTGGCACT ATAATGTAAG CTCTACTGAG GTGCTATGTT CTTAGTGGAT         644

GTTCTGACCC TGCTTCAAAT ATTTCCCTCA CCTTTCCCAT CTTCCAAGGG TACTAAGGAA         704

TCTTTCTGCT TTGGGGTTTA TCAGAATTCT CAGAATCTCA AATAACTAAA AGGTATGCAA         764

TCAAATCTGC TTTTTAAAGA ATGCTCTTTA CTTCATGGAC TTCCACTGCC ATCCTCCCAA         824

GGGGCCCAAA TTCTTTCAGT GGCTACCTAC ATACAATTCC AAACACATAC AGGAAGGTAG         884

AAATATCTGA AAATGTATGT GTAAGTATTC TTATTTAATG AAAGACTGTA CAAAGTATAA         944

GTCTTAGATG TATATATTTC CTATATTGTT TTCAGTGTAC ATGGAATAAC ATGTAATTAA        1004

GTACTATGTA TCAATGAGTA ACAGGAAAAT TTTAAAAATA CAGATAGATA TATGCTCTGC        1064

ATGTTACATA AGATAAATGT GCTGAATGGT TTTCAAATAA AAATGAGGTA CTCTCCTGGA        1124

AATATTAAGA AAGACTATCT AAATGTTGAA AGATCAAAAG GTTAATAAAG TAATTATAAC        1184

T                                                                       1185
```

( 2 ) INFORMATION FOR SEQ ID NO:6:

( i ) SEQUENCE CHARACTERISTICS:
        ( A ) LENGTH: 98 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Asn Gln Thr Ala Ile Leu Ile Cys Cys Leu Ile Phe Leu Thr Leu
 1               5                  10                  15

Ser Gly Ile Gln Gly Val Pro Leu Ser Arg Thr Val Arg Cys Thr Cys
            20                  25                  30
```

```
Ile  Ser  Ile  Ser  Asn  Gln  Pro  Val  Asn  Pro  Arg  Ser  Leu  Glu  Lys  Leu
          35                      40                      45

Glu  Ile  Ile  Pro  Ala  Ser  Gln  Phe  Cys  Pro  Arg  Val  Glu  Ile  Ile  Ala
          50                      55                      60

Thr  Met  Lys  Lys  Lys  Gly  Glu  Lys  Arg  Cys  Leu  Asn  Pro  Glu  Ser  Lys
65                       70                      75                            80

Ala  Ile  Lys  Asn  Leu  Leu  Lys  Ala  Val  Ser  Lys  Glu  Met  Ser  Lys  Arg
               85                      90                           95

Ser  Pro
```

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Gly  Ser  Ser  Gly
 1
```

( 2 ) INFORMATION FOR SEQ ID NO:8:

( i ) SEQUENCE CHARACTERISTICS:
        ( A ) LENGTH: 4amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Arg  Ser  Ser  Gly
 1
```

MODULATION OF ENDOTHELIAL CELL PROLIFERATION WITH IP-10

BACKGROUND OF THE INVENTION

The field of the invention is regulation of endothelial cell proliferation in mammals.

IP-10 was identified as an abundant RNA induced by interferon-gamma and lipopolysaccharide and encodes a 10 Kda secreted protein. It is a member of the —C—X—C— (or α) chemokine family of secreted 8–10 Kda proteins and is 31% identical to platelet factor 4 (PF4) and 26% identical to interleukin 8 (IL-8), two other members of the —C—X—C— chemokine family. IP-10 expression is induced in a variety of tissues in inflammatory conditions, such as psoriasis, fixed drug eruptions, cutaneous delayed-type hypersensitivity reactions, experimental glomerulonephritis and in experimental allergic encephalomyelitis.

IP-10 may be a chemoattractant for T cells and monocytes and may induce T cells to adhere to activated endothelial cells, although these latter in vitro findings remain controversial. Chemokine receptors are known to be promiscuous, binding more than one chemokine, and various leukocytes are known to have more than one chemokine receptor, making interpretation of binding data difficult. The recent molecular cloning of several chemokine receptors, including IL-8 type A and B, MIP1α/RANTES, MCP-1, and the erythrocyte chemokine receptor, and the demonstration of binding and signaling in heterologous cells has been important in clarifying receptor-ligand interactions. All the chemokine receptors cloned to date are members of the G-protein coupled seven transmembrane spanner family, and, with the exception of the promiscuous erythrocyte chemokine receptor (which is the Duffy blood group antigen), induce transient rises in intracellular calcium upon activation. However, to date, a signaling receptor has not been identified for several chemokines, including IP-10 and the first chemokine to be identified, PF4.

PF4 has been shown to bind to cell-surface heparan sulfate proteoglycans (HSPG) and may, in fact, exert its biological effects of tumor inhibition and angiostasis by displacing growth factors such as basic fibroblast growth factor (bFGF) and transforming growth factor β (TGF-β), which utilize TGF-β cell-surface HSPG as part of their receptor complexes.

SUMMARY OF THE INVENTION

In general, the invention features a method of inhibiting endothelial cell proliferation in a mammal. This inhibition may be achieved by administering an endothelial cell-inhibiting amount of IP-10 polypeptide to the mammal or by administering a nucleic acid encoding an IP-10 polypeptide to the mammal.

For example, IP-10 may be administered to treat (e.g., halt or slow the progression of) a condition involving endothelial cell proliferation, or to prevent the occurrence of such a condition. In preferred embodiments, the mammal is a human. In other embodiments, the IP-10 is naturally occurring IP-10 or an IP10-AP fusion protein. In various other preferred embodiments, the endothelial cell being inhibited is a cell of an endothelioma (e.g., a Karposi's sarcoma, a sclerosing endothelial sarcoma, or a hemangioma). The endothelial cell may be an endothelial cell capable of tumor angiogenesis, in which case the method may be used to inhibit the endothelial cell proliferation required to support tumor formation. In another embodiment, the method may be used for the treatment of arteriosclerosis (e.g., atheriosclerotic lesions).

In a second aspect, the invention features a method of increasing endothelial cell proliferation in a mammal by decreasing IP-10 binding to an HSPG receptor. In preferred embodiments endothelial cell proliferation is increased for the purpose of treating traumatic injury or ischemic injury (e.g., myocardial infarction, cerebral vascular accident, pulmonary embolus, retinal artery necrosis, or acute renal failure). In other preferred embodiments IP-10 receptor binding may be decreased by the administration of a therapeutically effective dosage of one or more of the following: heparin, heparan sulfate, fragments of IP-10 (e.g., the 25 carboxy terminal amino acids of IP-10) an antibody which specifically binds IP-10, or an antibody which specifically binds the HSPG receptor.

In a third aspect, the invention provides a method of preventing chemokine aggregation. The method includes constructing a fusion protein whereby chemokine polypeptide sequences are covalently linked to the alkaline phosphatase polypeptide sequences. The fusion protein covalent linkage is such that the fusion protein has decreased aggregation relative to the naturally occurring chemokine from which the chemokine sequences are derived. The alkaline phosphatase may be linked to either the amino terminus or carboxy terminus, but is preferably linked to the carboxy terminus of the chemokine. In preferred embodiments the chemokine may be IP-10, RANTES, MIP-1β, or PF4. In a related aspect the invention features chemokine fusion proteins with decreased aggregation.

In a fifth aspect, the invention features a method of detecting a compound which alters IP-10 binding to cells. The method includes combining a cell, the IP10-AP polypeptide, and the compound to be tested under conditions which allow binding of the IP10-AP to the cell absent a test compound. Alkaline phosphatase activity is then measured and a change in the alkaline phosphatase activity indicates a compound which modulates IP-10 binding to the HPSG receptor. In a preferred embodiment, the compound is further tested for its ability to inhibit endothelial cell proliferation. For this purpose and others, the ability of a peptide or compound to modulate endothelial cell proliferation may be tested by using the in vivo and in vitro assays described herein. Preferably, the assay used is the HUVEC proliferation assay provided in the examples.

In a sixth aspect, the invention features a method of inhibiting FGF in a mammal by the administration of a therapeutically effective amount of IP-10 polypeptide, or IP-10 encoding nucleic acid. In preferred embodiments IP-10 is administered for the inhibition of a hemangioma, a neoplasm having increased levels of FGF (e.g, a Karposi's sarcoma, a keloid, or a proliferative retinal disorder.

In a related aspect, the invention features a method of inhibiting TGFβ, by administering a therapeutically effective amount of IP-10 polypeptide or IP-10 encoding nucleic acid. In preferred embodiments, IP-10 is administered to inhibit TGFβ in mammals diagnosed with or at risk for unresolved fibrotic inflammation or a neoplasm with increased levels of TGFβ.

In general, where IP-10 is provided as a polypeptide, it may be in a pharmaceutically acceptable carrier and/or may be administered by localized injection, by continuous release, or by intravenous injection. Where the IP-10 is provided by transformation of the mammal's cells with IP-10 encoding nucleic acid, the nucleic acid may be provided via a viral vector in one preferred embodiment.

By "IP-10 gene" is meant a gene encoding an IP-10 polypeptide. An IP-10 gene is a cytokine gene having about 50% or greater sequence identity to the IP-10 sequence of FIG. 11 (SEQ ID No. 6) or a portion thereof. For example, the gene may encode human or murine IP-10 polypeptide.

By "polypeptide" is meant any chain of amino acids, regardless of length or post-translational modification (e.g., glycosylation or phosphorylation).

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

By a "substantially pure polypeptide" is meant an IP-10 polypeptide (or other polypeptide described herein) which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, IP-10, IP10-AP, or another polypeptide which is used in the methods of the invention. A substantially pure polypeptide may be obtained, for example, by extraction from a natural source (e.g., a mammalian cell); by expression of a recombinant nucleic acid encoding an the polypeptide; or by chemically synthesizing the protein. Purity can be measured by any appropriate method, e.g., those described in column chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

By "decreased aggregation" is meant a decrease in self-aggregation under conditions of physiological pH and tonicity. A decrease in aggregation may be assayed by assaying a biological activity such as receptor binding. Example 4, below, demonstrates such an assay.

By "HSPG receptor" is meant a cell surface moiety having heparan sulfate proteoclycans. Preferably, the HSPG receptor is a moiety to which IP-10 specifically binds. More preferably the HSPG receptor is the receptor described in the examples below.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) a polypeptide described herein (for example, an IP-10 or IP10-AP polypeptide).

By "positioned for expression" is meant that the DNA molecule is positioned adjacent to a DNA sequence which directs transcription and translation of the sequence (i.e., facilitates the production of, e.g., an IP-10 polypeptide, a recombinant protein or a RNA molecule).

By "fusion protein" is meant a hybrid polypeptide which includes functional portion of a protein whose presence may be assayed; such portions include, without limitation, alkaline phosphatase, β-glucuronidase (GUS), luciferase, chloramphenicol transacetylase (CAT), and β-galactosidase. Preferably, the portion includes a functional fragment from the alkaline phosphatase protein.

By "IP10-AP" is meant a fusion protein which includes amino acid sequences from both the IP-10 polypeptide and the alkaline phosphatase (AP) polypeptide. Preferably, the fusion protein has both AP biological activity and IP-10 biological activity. Most preferably the fusion is the protein described in FIG. 3A and FIG. 3B.

By "biological activity" is meant those activities which may be attributed to the naturally occurring protein both in vivo and in vitro. For example, IP-10 has biological activities which include binding to HSPG receptors, inhibiting endothelial cell proliferation and inhibiting tumor formation.

By "promoter" is meant minimal sequence sufficient to direct transcription. Also included in the invention are those promoter elements which are sufficient to render promoter-dependent gene expression controllable for cell-type specific, tissue-specific or inducible by external signals or agents; such elements may be located in the 5' or 3' regions of the native gene.

By "operably linked" is meant that a gene and a regulatory sequence(s) are connected in such a way as to permit gene expression when the appropriate molecules (e.g., transcriptional activator proteins) are bound to the regulatory sequence(s).

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous or even identical to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic plants and the DNA (transgene) is inserted by artifice into the nuclear or plastidic genome.

By "conserved region" is meant any stretch of six or more contiguous amino acids exhibiting at least 30%, preferably 50%, and most preferably 70% amino acid sequence identity between two or more of the IP-10 family members.

By "transformation" is meant any method for introducing foreign molecules into a cell. For example, molecules may be introduced using velocity driven microprojectiles such as tungsten or gold particles, electroporation, viral insertion, or liposome delivery. Velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (e.g., chloroplasts and mitochondria), bacteria, yeast, fungi, algae, and animal tissue.

By "purified antibody" is meant antibody which is at least 60%, by weight, free from proteins and naturally-occurring organic molecules with which it is naturally associated. Preferably, the preparation is at least 75%, more preferably 90%, and most preferably at least 99%, by weight, antibody, e.g., an IP-10-specific antibody. A purified IP-10 antibody may be obtained, for example, by affinity chromatography using recombinantly-produced IP-10 protein or conserved motif peptides and standard techniques.

By "an antibody which specifically binds" is meant an antibody which recognizes and binds an IP-10 protein or an HSPG receptor but which does not substantially recognize and bind other molecules in a sample, e.g., a biological sample, which naturally includes IP-10 protein and/or the HSPG receptor.

By "specifically binds the HSPG receptor" is meant a polypeptide or other compound which recognizes and binds the HSPG receptor but which does not substantially recognize and bind other molecules in a sample, e.g., a biological sample, which naturally includes the HSPG receptor. Preferably, a polypeptide or other compound which binds the HSPG receptor has a Kd of 1 $\mu$M, or less; more preferably, 100 nM, even more preferably, 25 nM; and most preferably, 100 nM.

By "endothelial cell" is meant a cell of the endothelium. For example the flat cells lining the blood vessels lymphatic vessel and the heart are endothelial cells. Preferably, the endothelioma is a Karposis sarcoma or an hemangiomer.

By "endotheliosis" is meant proliferation of endothelial cells.

By a "endothelioma" is meant an endothelial cell which has been released from normal cell division control. Included in this definition are transformed and immortalized endothelial cells. Preferably, the endothelioma is a Karposi's sarcoma or an hemangioma.

By "inhibiting endothelial cell proliferation" is meant any decrease in the degree of proliferation of the endothelial cells being treated. It will be appreciated that any decrease is therapeutically useful in the neoplastic and arterial sclerosis clinical situations. Preferably, the decrease is 20%, more preferably the decrease is 50%, and most preferably the decrease is 95% relative to cells not treated with IP-10.

By "increasing endothelial cell proliferation" is meant any increase in the degree of proliferation of the endothelial cells being treated. It will be appreciated that any increase is therapeutically useful in the myocardial infarction, traumatic injury, and ischemia clinical situations. Preferably, the increase is 50%, more preferably the increase is 2-fold, and most preferably the increase is 5-fold relative to cells not treated with IP-10.

Other features and advantages of the invention will be apparent from the following detailed description thereof, and from the claims.

DETAILED DESCRIPTION

The drawings will first be described.

Drawings

Figure 1A:
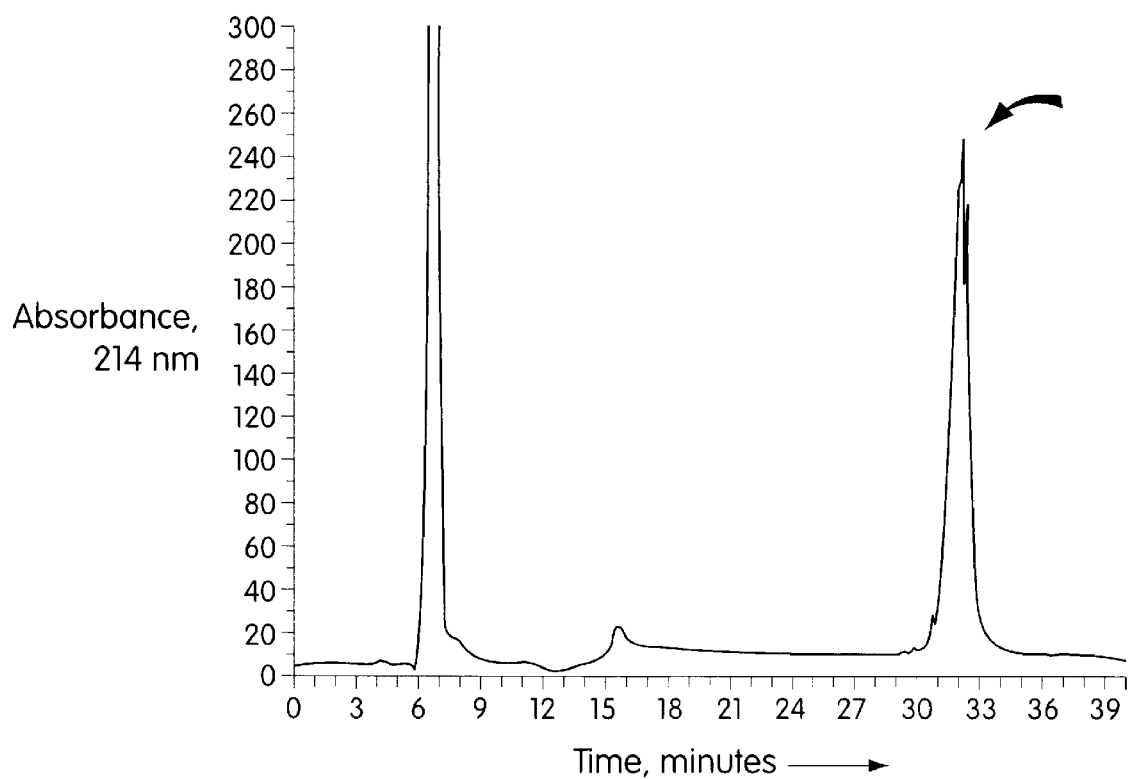
Figure 1B:
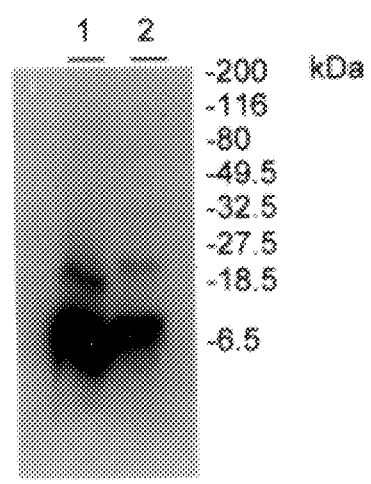

FIGS. 1A and 1B show the expression and purification of E. coli rIP-10. FIG. 1A shows reverse phase HPLC purification of rIP-10. Curved arrow indicates position of IP-10 on A214 chromatogram. The first peak that is off scale is the urea loading buffer. FIG. 1B shows 12.5% SDS-PAGE (Tris/Tricine) analysis of Bolton and Hunter 125I-labeled rhIP-10. Lane 1 is $^{125}$I labeled PeproTech human IP-10 (NEN/Dupont) and lane 2 is the 6 his-tagged hIP-10 shown in FIG. 1A. Molecular weight markers in Kda are indicated to the right of the gel.

Figure 2A:
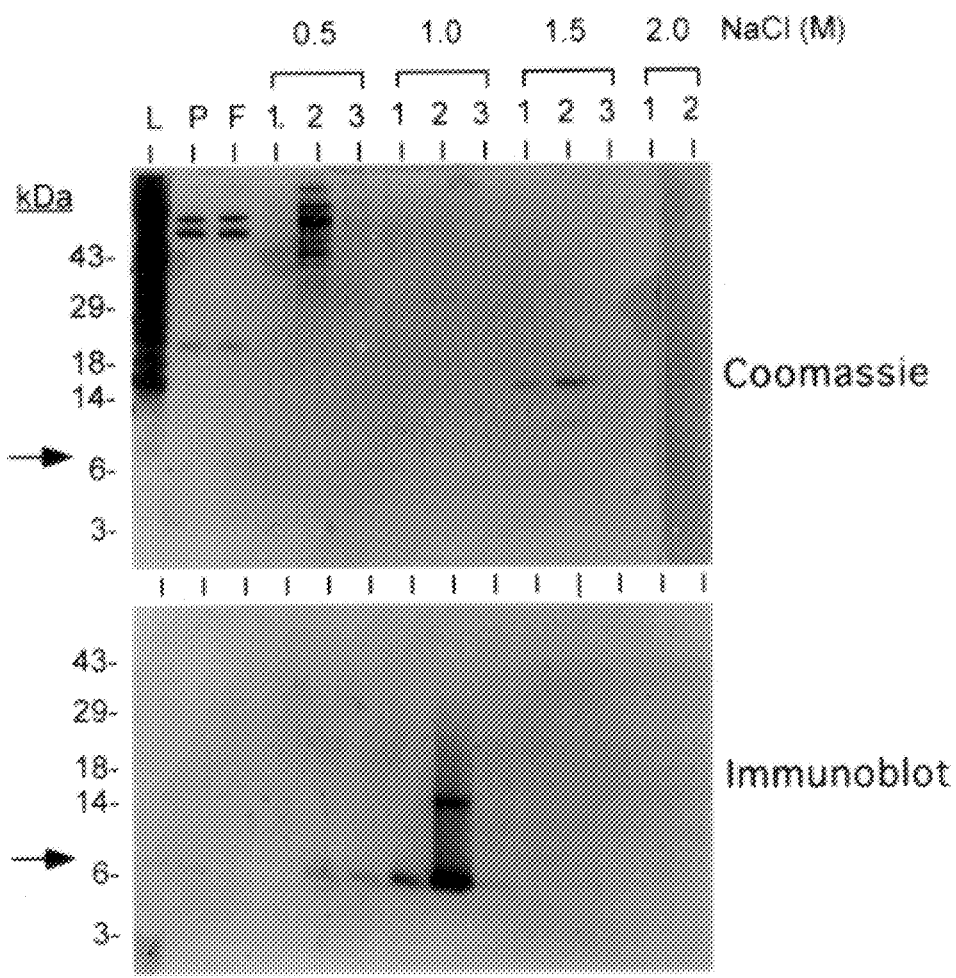
Figure 2B:
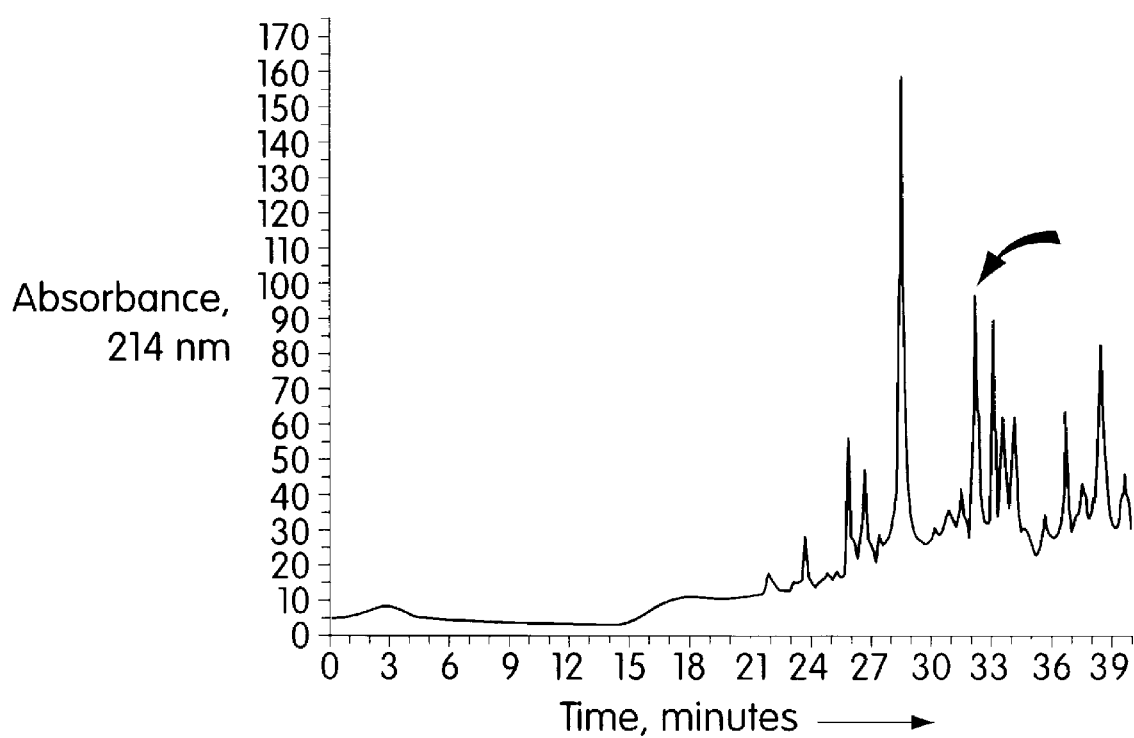
Figure 2C:
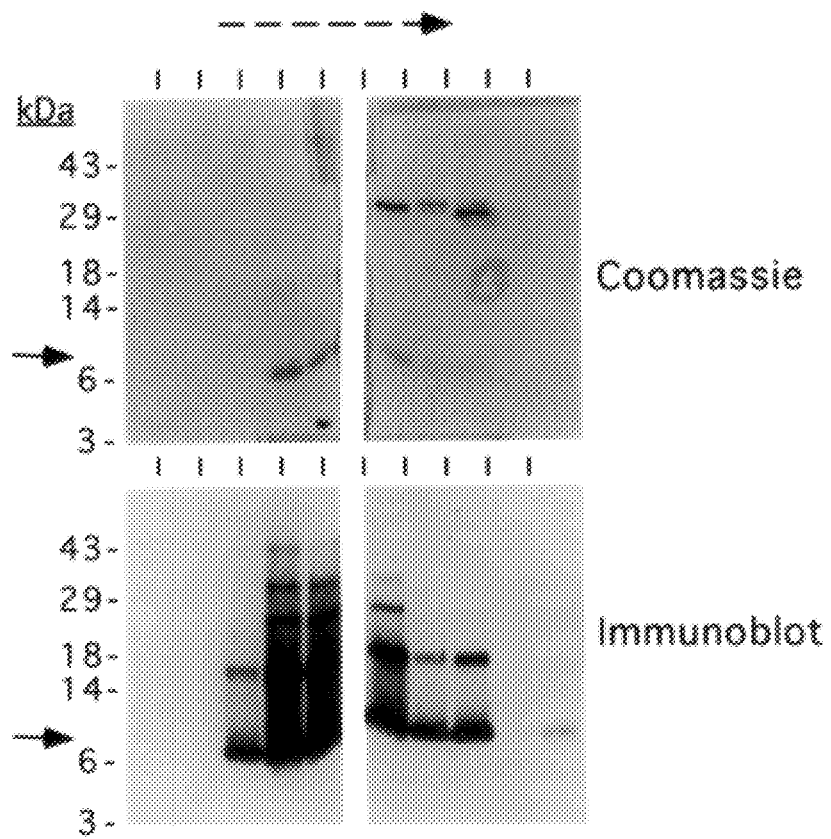

FIGS. 2A–2C show purification of recombinant IP-10 secreted from J558L cells. FIG. 2A is heparin Sepharose affinity chromatography of serum-free conditioned medium collected from J558L cells transfected with a human IP-10 cDNA expression construct analyzed by reverse phase HPLC. Top panel—Coomassie stained 12.5% SDS-PAGE (Tris/Tricine) of fractions eluted step-wise from a heparin Sepharose column with the indicated concentrations of NaCl. Bottom panel—Immunoblot of equivalent gel stained with affinity purified rabbit anti hIP-10 antibody. L-cell lysate, P-precolumn, F-column flow through. Numbers 1,2,3 represent sequential fractions collected at the NaCl concentration indicated above the number. FIG. 2B shows reverse phase HPLC profile of 1M NaCl eluate from heparin Sepharose column. FIG. 2C shows 12.5% SDS-PAGE of HPLC fractions shown in FIG. 2B. Top panel—Coomassie stained gel, bottom panel—immunoblot using affinity purified rabbit anti-IP10 antiserum. Dotted arrow indicates direction of increasing acetonitrile concentration. Solid arrows indicate position of monomeric IP-10. Molecular weight markers in Kda are indicated to the right of the gel. Curved arrow in FIG. 2B indicates the IP-10 peak as determined by immunoblot of HPLC factions shown in FIG. 2C.

Figure 3A:
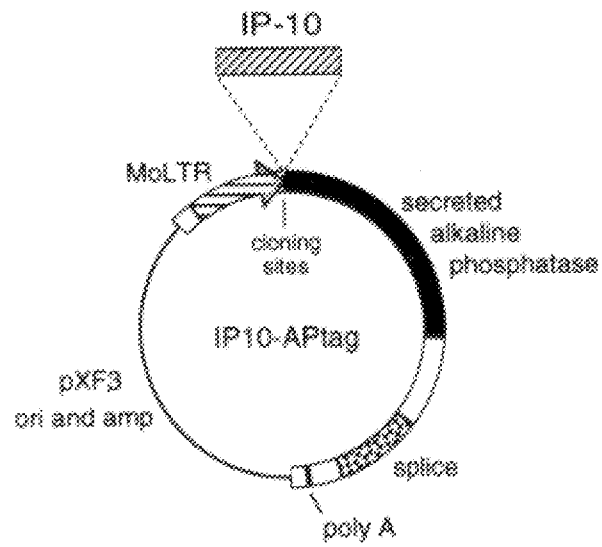
Figure 3B:

FIGS. 3A and 3B show alkaline phosphatase fusion protein (IP10-AP). FIG. 3A shows a schematic of mammalian expression vector APtag. FIG. 3B shows the result when conditioned medium from NIH-3T3 cells transfected with vector of FIG. 3A is immunoprecipitated using a monoclonal antibody to alkaline phosphatase, subjected to 10% SDS-PAGE and then immunoblotted with rabbit anti-murine IP-10 antibody.

Figure 4A:
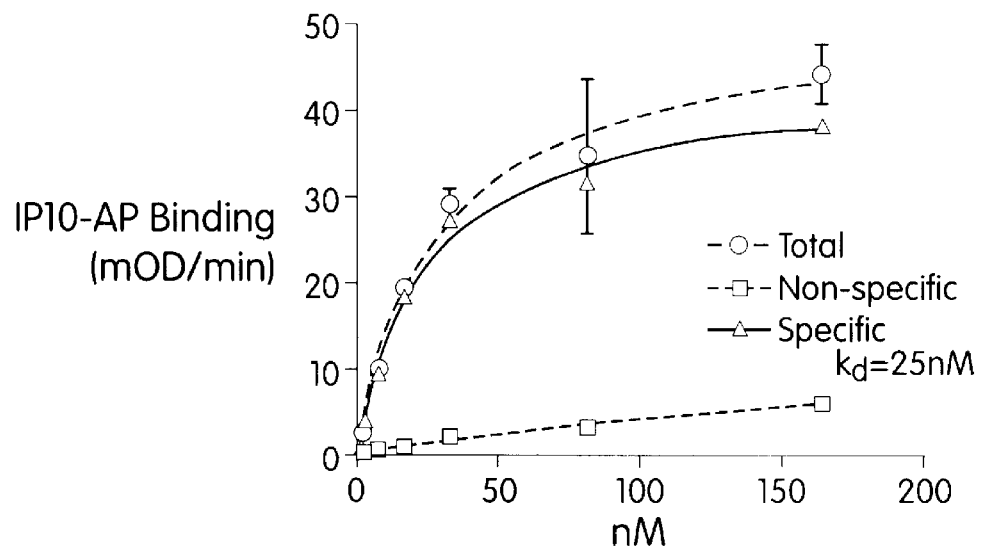
Figure 4B:
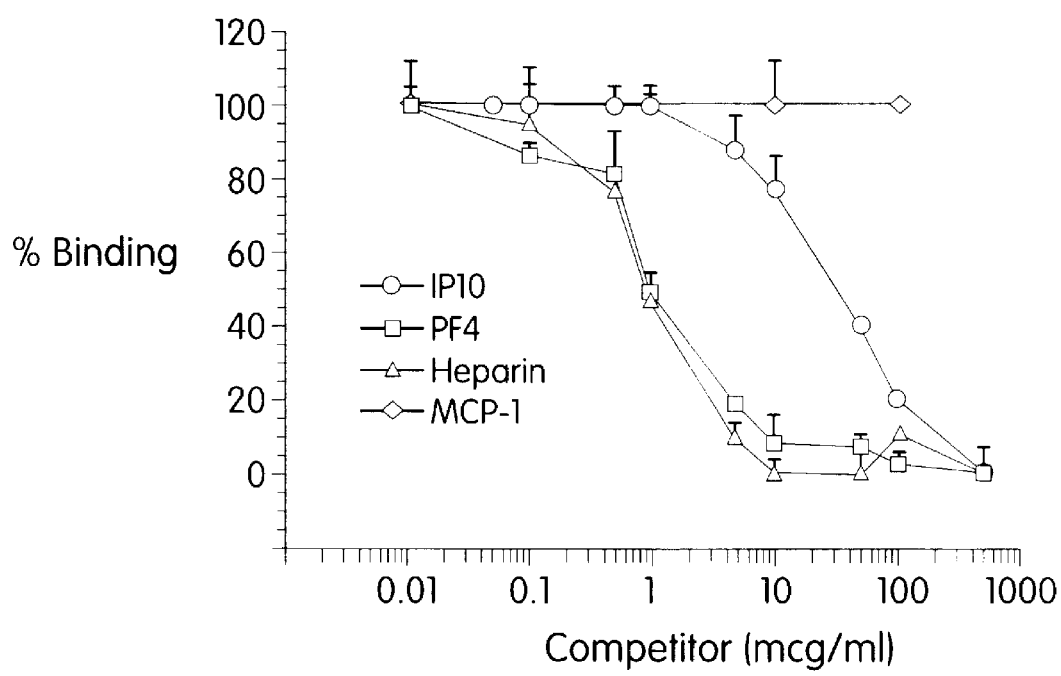

FIGS. 4A and 4B demonstrate that IP10-AP binding is specific, saturable and competed by PF4 and heparin. FIG. 4A shows IP10-AP binding to A20 B cells. Specific binding= (total binding)−(non-specific) at each point. FIG. 4B shows concentration-dependent inhibition. Data is presented as the % binding=(Binding in presence of competitor minus non-specific binding)/(Binding in the absence of competitor minus non-specific binding)×100.

Figure 5:
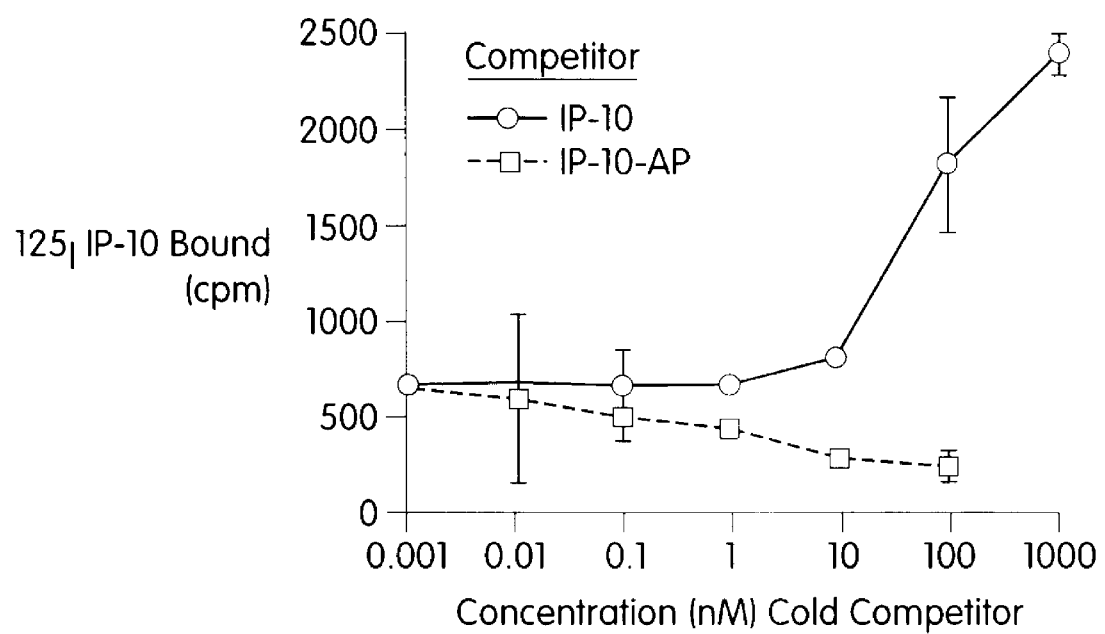

FIG. 5 shows IP10-AP inhibits aggregation of IP-10 on cell surfaces.

Figure 6A:
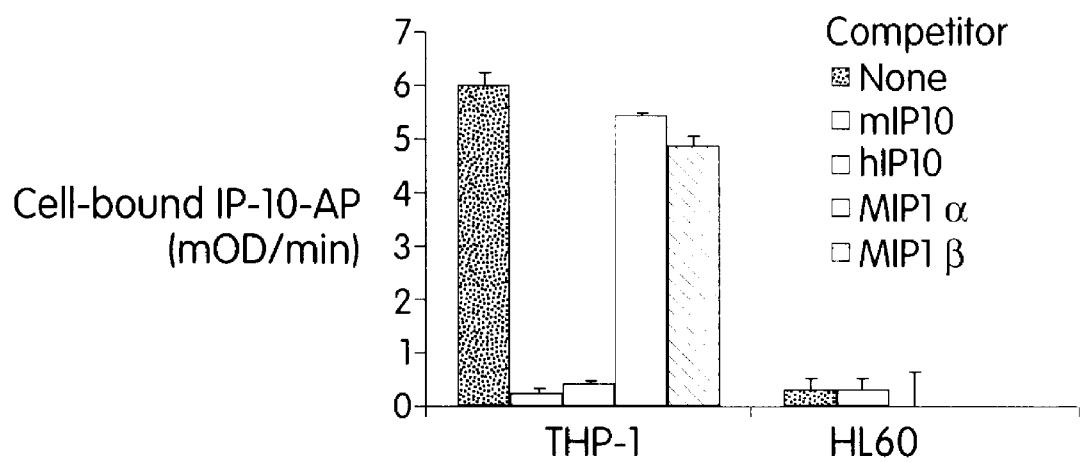
Figure 6B:
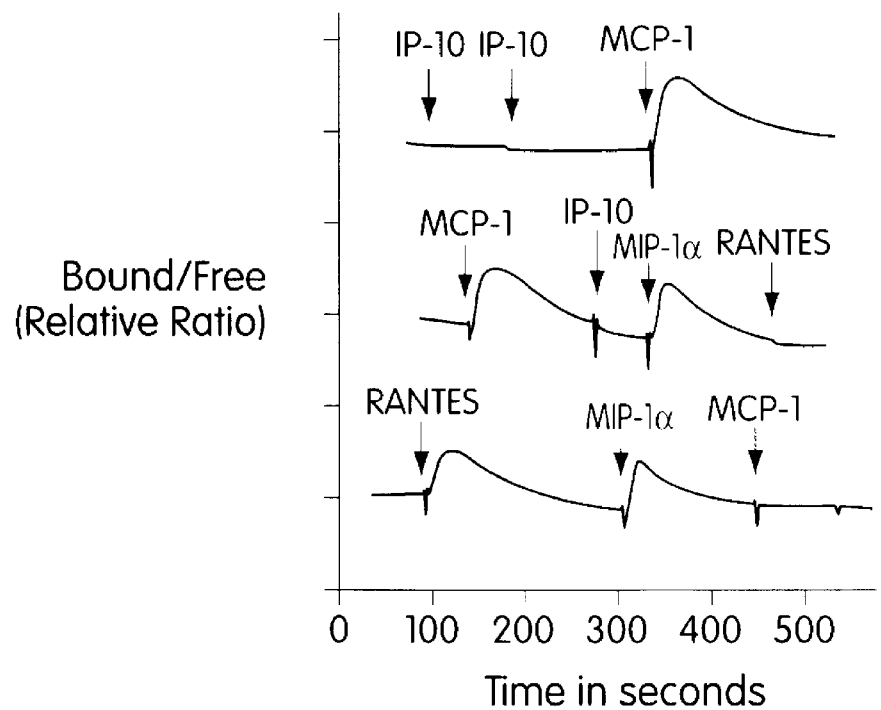

FIGS. 6A and 6B demonstrate IP-10 binds to the chemokine responsive THP-1 cell line, but does not induce a detectable intracellular calcium flux. FIG. 6A shows specific binding. 107 THP-1 or HL60 cells were incubated for 2 hours at 4° C. with 15 nM IP10-AP in the presence of various competitors: (None); human (h) and murine (m) IP-10; MIP-1a and MIP-1b (THP-1 cells only). The cells were then washed 5× with HBSS binding buffer, and assayed for cell-bound alkaline phosphatase activity. FIG. 6B shows the calcium flux. THP-1 cells were loaded with Fura-2 and assayed by spectrophotometric methods at 37° C. with continuous stirring. Addition of indicated recombinant human chemokine to THP-1 cells is illustrated by arrow. All chemokines were added to a final concentration of 10 nM except for the second addition of IP-10 which was added to 100 nM.

Figure 7:
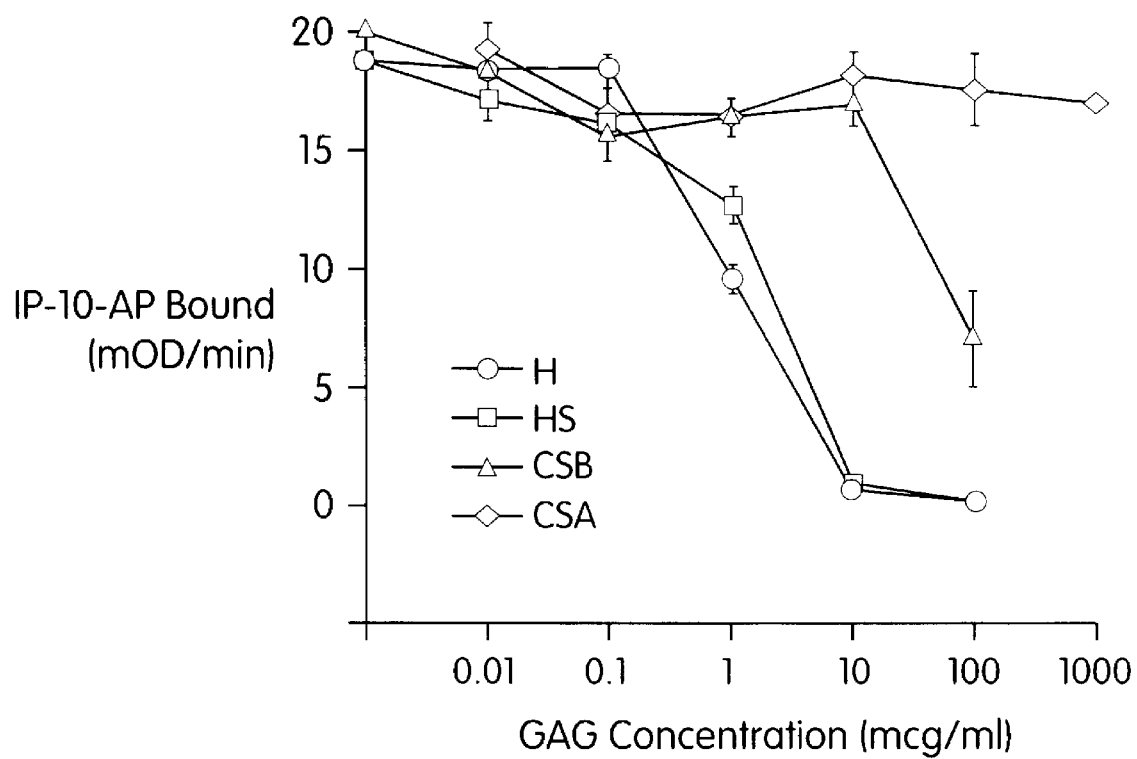

FIG. 7 demonstrates glycosaminoglycan inhibition of IP10-AP binding to A20 cells. 107 A20 cells were incubated with 15 nM mIP10-AP in the presence of the indicated concentrations of heparin (H), heparan sulfate (HS), chondroitin sulfate B (CSB) and chondroitin sulfate A (CSA) for 2 hours on ice. Cells were then washed and bound IP10-AP assayed.

Figure 8A:
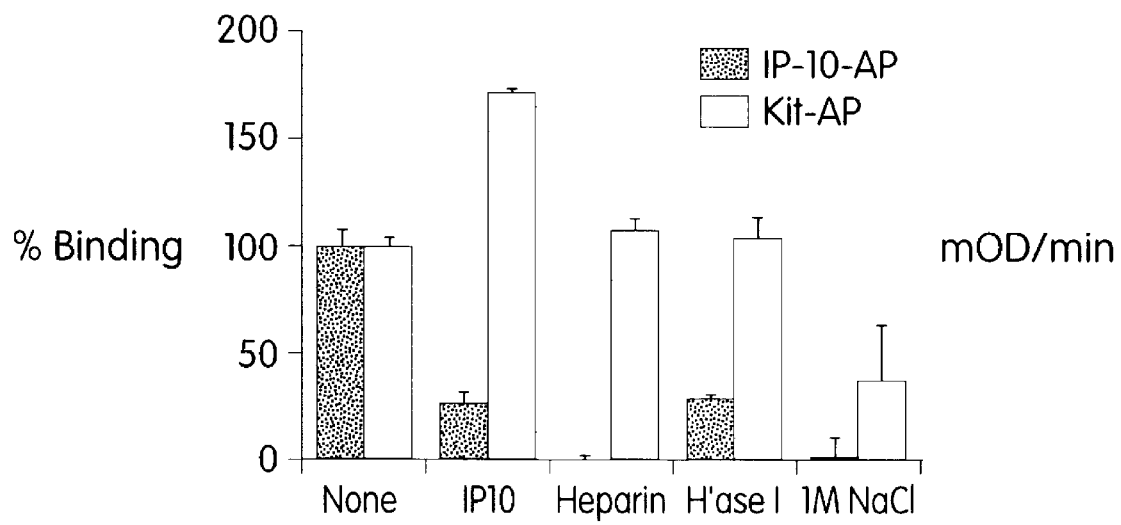
Figure 8B:
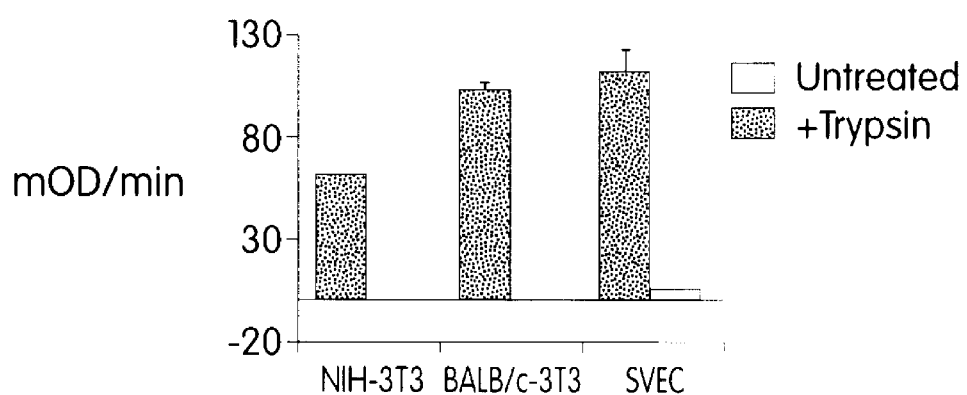

FIGS. 8A and 8B demonstrate that the IP-10 binding site is heparinase, salt, and trypsin sensitive. FIG. 8A shows the result when 106 Balb/c-3T3 cells are incubated with either 15 nM mIP10-AP or an equivalent amount of kit-AP in the presence of no competitor (None), 1 mM mIP-10, or 100 mg/ml heparin for 2 hrs at 4° C. FIG. 8B shows the result when 107 cells are trypsinized with 0.25% Trypsin/1 mM EDTA for 5 minutes at room temperature after which they were incubated with 15 nM mIP10-AP for 2 hours at 4° C., washed 5× with HBSS binding buffer, and assayed for bound alkaline phosphatase activity. Binding was determined in parallel on an equivalent number of untrypsinized cells. SVEC is an SV40 transformed murine endothelial cell line.

Figure 9:
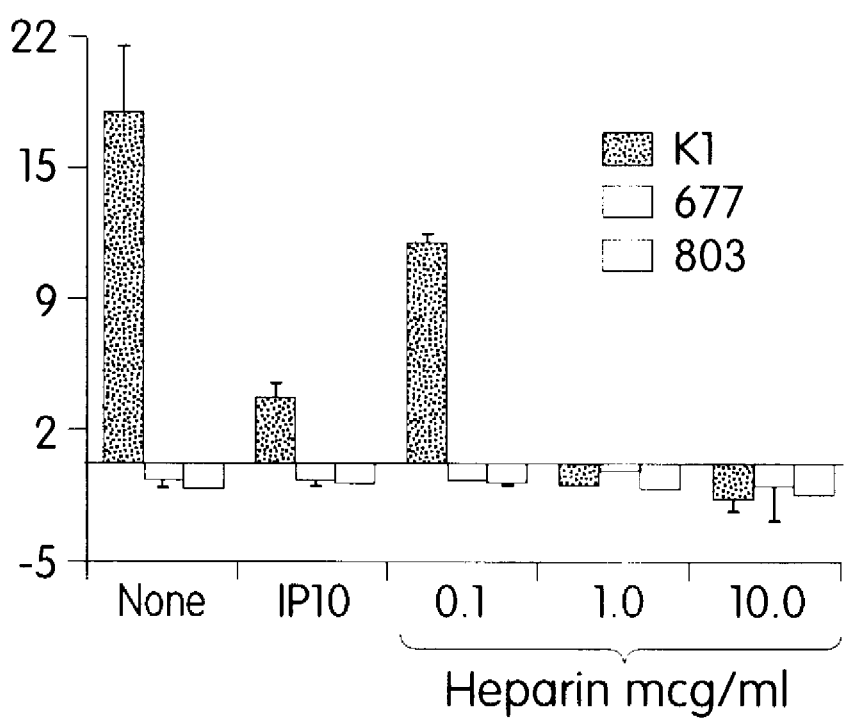

FIG. 9 demonstrates IP10-AP binds to wild-type CHO (K1) cells but does not bind to the heparan sulfate deficient mutant CHO cells (677 and 803).

Figure 10A:
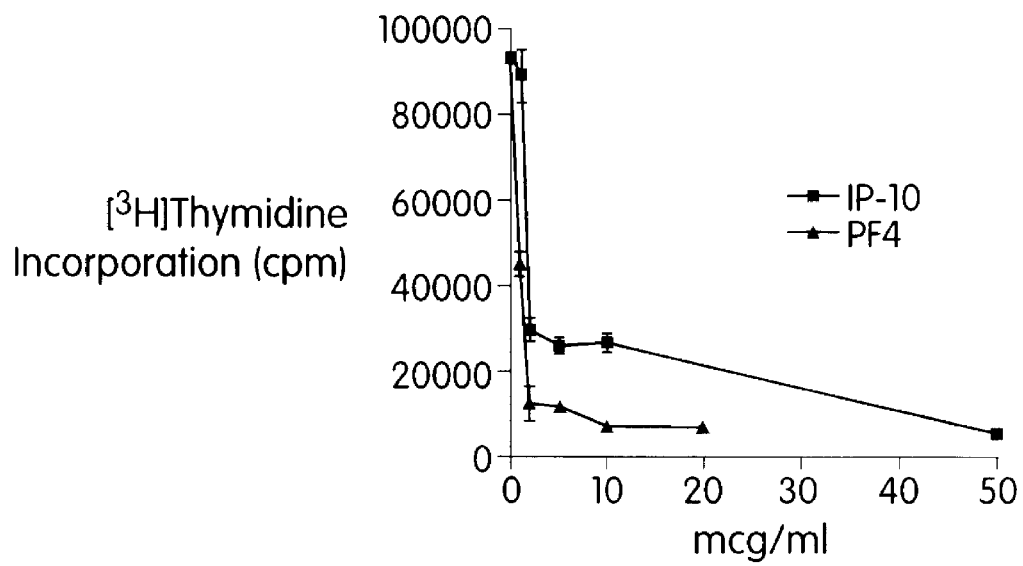
Figure 10B:
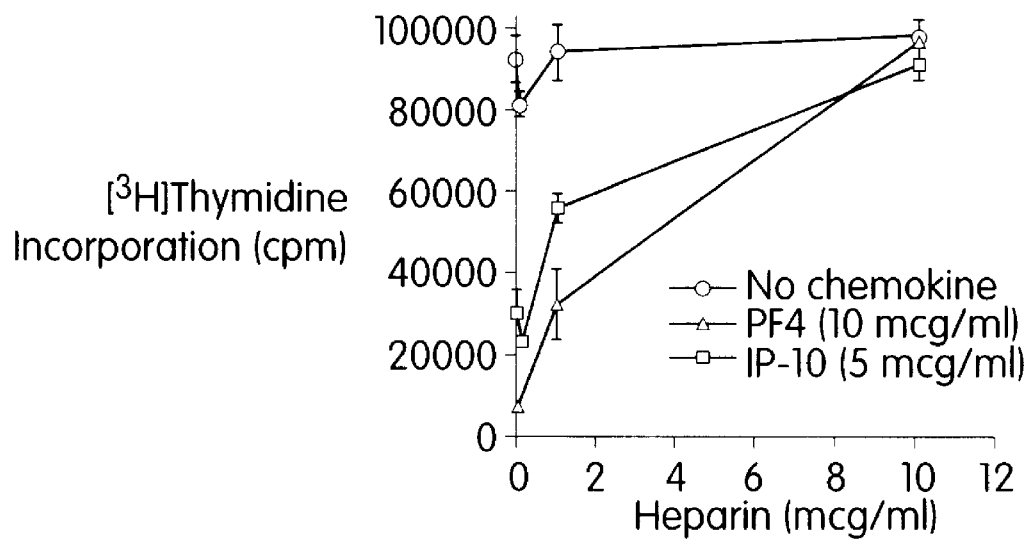

FIGS. 10A and 10B demonstrate IP-10 inhibits endothelial proliferation—an effect that is antagonized by heparin. FIG. 10A shows human umbilical cord vein endothelial cells (HUVEC's) were plated in triplicate in a 96 well plate in the presence of the indicated concentration of hIP-10 or hPF4, 5 ng/ml bFGF and 10% FBS. The amount of [3H]-thymidine incorporated into each well was determined on day 3. FIG. 10B shows the result when 6×103 HUVECs were plated with the bFGF containing media and with the indicated concentration of heparin alone or with heparin plus 5 mg/ml IP-10 or 10 mg/ml of PF4 for 3 days and the amount of [3H]-thymidine over that period determined.

FIG. 11 shows the human IP-10 polypeptide (SEQ. ID No. 5) and nucleic acid (SEQ ID No. 6) sequences.

I. INTRODUCTION

One of the major problems in studying the properties of IP-10 has been that, like other chemokines, (Lodi, P. J. et al. 1994. Science 263: 1762–1767; Mantel, C. et al. 1993. Proc. Natl. Acad. Sci. USA 90: 2232–2236), IP-10 self-aggregates at physiological pH and tonicity. This aggregation has interfered with identification of a specific and saturable IP-10 cellular binding site. To overcome this problem, we have now generated an IP-10 alkaline phosphatase fusion protein that retains its ability to bind to cells, but does not aggregate in physiological buffers. Using this fusion protein, we have now demonstrated that IP-10 binds to a cell-surface heparan sulfate proteoglycan (HSPG) receptor with a Kd of 25 nM. The conclusion that this receptor is a HSPG receptor rests on the observations that cellular IP-10 binding is inhibited by heparin and heparan sulfate, that it is eliminated by treatment with heparinase and trypsin, and that it is absent on mutant CHO cells that do not express cell-surface HSPG.

The binding of IP-10 to its HSPG receptor is a specific interaction. Only PF4 and certain glycosaminoglycans compete for IP-10 binding to cells. Heparin and heparan sulfate are equipotent in competing for IP-10 binding sites, while chondroitin sulfate B is at least 100 fold less potent and chondroitin sulfate A is unable to compete for these sites. Further, PF4 is as potent as heparin in competing with IP-10 binding to cells, while IL-8, RANTES, MIP-1a, MIP-1b and MCP-1 have virtually no inhibitory effect on IP-10. Although IL-8 binds heparin and is almost as homologous to IP-10 as PF4 (26% vs. 31%), it does not effectively compete for IP-10's cellular HSPG sites. Interestingly, we have found that human and murine IP-10 competed with murine IP10-AP and with human IP10-AP for cellular binding, suggesting that there is no difference in binding specificity among these species (i.e., murine and human IP-10 may be used interchangeably). It is also striking that IP-10 is less potent on a weight basis than either PF4 or heparin in competing with IP10-AP binding. This observation is consistent with the formation of IP-10 aggregates, decreasing its effective molar concentration. Aggregation may also explain the four fold lower Kd found for IP-10 binding to soluble heparin as compared with IP10-AP binding to cells. Since the monomeric fusion protein IP-10 binds to cells, aggregation of IP-10 is not required for binding to its HSPG receptor. Our approach of using a fusion protein to inhibit self-aggregation, may be used with other chemokines.

We have also demonstrated that IP-10 inhibits bFGF induced proliferation of endothelial cells. Moreover, heparin antagonizes this inhibition, suggesting that the antiproliferative effect of IP-10 is mediated through this same HSPG receptor. The specific HSPG site that PF4 and IP-10 share may be a physiologically relevant site at which these molecules modulate the action of other cytokines that utilize HSPG as part of their receptor complex. For example, PF4 can inhibit both bFGF (Sato, Y. et al. 1990. Biochemical & Biophysical Research Communications 172: 595–600) and TGFb (Whitson, R. H. et al. 1991. Journal of Cellular Biochemistry 47: 31–42) binding to cells. Indeed, this may be the mechanism whereby PF4 and IP-10 exert their antiproliferative effects and may explain the growth regulating properties that the chemokines have on many diverse cell types.

Our results do not exclude the possibility that there is another receptor for IP-10. Nonetheless, we were unable to detect an IP-10 binding site on human peripheral lymphocytes even though it has been reported that IP-10 is a chemotactic for peripheral blood T cells (Taub, D. D. et al. 1993. Journal Experimental Medicine 177: 1809–1814). Furthermore, we have been unable to detect a calcium flux in cells which specifically bind IP-10. It nonetheless remains formally possible that by fusing IP-10 to alkaline phosphatase, we have destroyed the ability of IP-10 to interact with its signaling receptor while preserving its ability to interact with a specific HSPG binding site. Although this is possible, other, albeit non-chemokine alkaline phosphatase fusion proteins (e.g., human and mouse IL4 (Morrison, B. W. and P. Leder. 1992. Journal of Biological Chemistry 267: 11957–11963.), kit (Flanagan, J. G. and P. Leder. 1990. Cell 63:185–194) and FGFR (Ornitz, D. M. et al. 1992. Molecular & Cellular Biology 12: 240–247) retain their ability to interact with their specific cell-surface receptor or ligands.

One other role for heparin and cell-surface HSPG is in enhancing signaling of cytokines to their signaling receptor chains. For example, FGF signaling through its tyrosine kinase receptor, FGFR1, requires either soluble or cell-surface bound HSPG. The HSPG receptor betaglycan is also involved in TGFb signaling. Betaglycan presents TGFb directly to the serine/threonine kinase-subunit of the signaling receptor, forming a high affinity ternary complex (Lopez-Casillas, F. et al. 1993. Cell 73: 1435–1444). It has been demonstrated that heparin and heparan sulfate enhance neultrophil responses to IL8 (Webb, L. M. et al. 1993. Proc Natl Acad Sci U.S.A. 90: 7158–7162) and augment the ability of MIP1b (Tanaka, Y. et al. 1993. Nature 361: 79–82) to induce T cell adhesion. The mechanism of this enhancement has not been examined and, indeed, it is not known whether cell-surface HSPG or soluble heparin is actually required for chemokines to bind to and signal through their seven transmembrane spanner receptors. This question could be experimentally approached by comparing the ligand binding and signaling properties of wild-type and HSPG deficient CHO cells that have been transfected with cloned chemokine receptors.

Chemokines are known to bind to heparin, and it has been proposed from studies that found immunoreactive MIP1b in the distribution of endothelial cells that they bind cell-surface HSPG (Tanaka, Y. et al. 1993. Nature 361: 79–82). Without wishing to bind ourselves, the following theory may be advanced. HSPG on cell surfaces may capture chemokines from the fluid phase, thereby immobilizing and establishing a gradient of chemokine that can then be presented to rolling leukocytes and perhaps serve as a substrate for chemotaxis or hapotaxis (Rot, A. 1992. Immunology Today 13: 291–294). The specificity of the chemokine-HSPG interaction may play a role in regulating leukocyte homing and the recruitment of leukocytes to sites of inflammation. This could be accomplished through the differential expression of specific HSPG on endothelial cells in different tissues, or through the induction of specific HSPG by specific inflammatory stimuli. The expression of HSPGs with affinity for only a subset of chemokines in a given microenvironment would then allow only those chemokines captured in that microenvironment to be presented to rolling leukocytes. Thus, those chemokines with affinity for the regionally expressed or induced HSPG would be able to more effectively deliver a signal to circulating leukocytes. This hypothesis has not been explored for the chemokines but the concept of HSPG-ligand specificity dictating a biological response has been established for the FGF family (Nurcombe, V. et al. 1993. Science 260; 103–106).

Constitutive expression of IP-10 is seen in the thymus and in the spleen and high levels of expression are seen in various inflammatory conditions. It is therefore possible that IP-10 plays an role in regulating immune and inflammatory responses by modulating the action of other cytokines that use HSPG as part of their receptor complex. Both IP-10 and PF4 have been demonstrated to inhibit the growth of tumors (see U.S. Ser. No. 07/935,587, filed Aug. 26, 1992, now U.S. Ser. No. 08/217,016, filed Mar. 23, 1994, incorporated herein by reference; Luster, A. D. and P. Leder. 1993. Journal of Experimental Medicine 178: 1057–1065; Sharpe, R. J. et al. 1990. Journal of the National Cancer Institute 82: 848–853), possibly through immunologic, inflammatory and/or angiostatic mechanisms. PF4 is, in fact, now in clinical trials as an antitumor agent. In preliminary experiments we have shown that injection of IP-10 into a tumor transplant site has an antitumor effect. In considering the pharmacological delivery of IP-10 or PF4 to tumors, one should bear in mind HSPG receptors may be expressed on the tumor cells themselves as well as on the endothelial and inflammatory cells that may be a part of the effector mechanism in the antitumor response.

II. USE OF IP-10 TO INHIBIT ENDOTHELIAL CELL PROLIFERATION

As noted above and demonstrated below (see, e.g., Example 9) IP-10 inhibits endothelial cell proliferation. Accordingly, IP-10 may be administered either directly as a polypeptide or via transfected nucleic acid, to inhibit such cellular proliferation. For example, endotheliomas may be treated by the administration of IP-10. In particular, Karposi's sarcoma and hemangioma progression may be inhibited by administering a dosage of IP-10 which decreases the rate of proliferation in the endothelial tissue. IP-10 may also be used to generally inhibit the vascularization required for tumor growth (for example, in sarcomas). IP-10 may also be used to inhibit the endothelial cell proliferation which occurs in arteriosclerosis.

In addition to inhibiting angiogenesis which accompanies an endothelioma, IP-10 may be administered to prevent, halt, or slow the angiogenesis required for other types of tumorigenesis. For example, IP-10 may be administered to inhibit angiogenesis in sarcomas.

Charges in the degree of endothelial cell proliferation may be determined using the in vivo matrigel assay (Passanitia, et al., Methods in Laboratory Investigation, 67:519 (1992)) or in vitro using the endothelial cell tube formation assay (Cid, M. et al. J. Clinical Invest., 91:977 (1993)); the cell migration assay (Pepper, et al., J. Cell Physiol., 153:129 (1992)); or the cell proliferation assay (see below).

The effectiveness of IP-10 polypeptides and analogs in treating Karposi's Sarcoma may be assayed using the βFGF mouse model (Ensoli et al., Nature, Vol. 371:674 (1994)).

III. USE OF IP-10 TO INCREASE ENDOTHELIAL CELL PROLIFERATION

An appreciation of IP-10's role in inhibiting endothelial cell proliferation provides methods for increasing endothelial cell proliferation by inhibiting IP-10 function. Enhancing vascularization is particularly beneficial for individuals who have suffered a loss of vascularization or whose tissues otherwise require enhanced blood flow. For example, patients who have suffered traumatic injury or ischemic injury (e.g., myocardial infarction, cerebral vascular accident, pulmonary embolus, retinal artery necrosis, or acute renal failure) will benefit from the administration of inhibitors of IP-10.

Preferably, the inhibitor of IP-10 is an inhibitor which decreases or prevents the binding of IP-10 to the HSPG receptor. For example, administration of heparin may be used to prevent the inhibition of endothelial cell proliferation normally caused by endogenous IP-10. Heparan sulfate may also be administered for this purpose. Antibodies to IP-10 or the HSPG receptor may also be employed.

Fragments of IP-10 which bind the receptor but lack other IP-10 biological activities may be used to inhibit IP-10 function. Preferably, a carboxy fragment is used, most preferably the last 25 amino acids of naturally occurring IP-10 polypeptide is used.

IV. ADMINISTRATION OF IP-10 TO BLOCK FGF AND TGFβ RECEPTOR BINDING

FGF and TGFβ are known to bind HSPG receptors. Accordingly, IP-10 may be administered to block receptor binding by these proteins. For example, IP-10 may be administered to block TGFβ action in unresolved inflammation and fibrotic events and in neoplastic growth events known to be regulated by TGFβ. Likewise, IP-10 may be administered to block FGF in situations such as infantile hemangioma, Karposi's sarcoma, Keloids and proliferative retinal disorders (such as diabetic retinopathy, and retrolental fibroplasia).

V. THERAPEUTIC ADMINISTRATION OF IP-10 POLYPEPTIDE

With the availability of the cloned gene, the substantially pure IP-10 polypeptide can be produced in quantity using standard techniques (see below, and Scopes, R. *Protein Purification: Principles and Practice* 1982 Springer-Verlag, NY). Thus, another aspect of the invention is a pharmaceutical comprising the IP-10 polypeptide together with an acceptable diluent, carrier or excipient and/or in unit dosage form. Conventional pharmaceutical practice may be employed to provide suitable formulations or compositions to administer the polypeptide to patients with endotheliomas, or for whom decreased endothelial proliferation is otherwise desirable.

As noted above, substantially pure preparation of a polypeptide is a preparation which is substantially free (e.g., to the extent required for formulating IP-10 into a therapeutic composition) of the proteins with which it naturally occurs in a cell.

Fragments or analogs of the IP-10 protein may also be administered to a patient in the manner described above. Fragments or analogs which are useful for this purpose include those which are described above and are useful for the treatment of a patient for whom decreased endothelial differentiation is advisable. Fragments and analogs which will be useful for the therapeutic treatment of patients are determined using the assays provided in the examples, below, among others.

The IP-10 polypeptide may also be administered to a patient in the form of a fusion protein consisting of an IP-10 polypeptide, fused to the a ligand or receptor protein, or a fragment thereof, which is sufficient to bind a receptor or a receptor ligand on the cell to which IP-10 may desirably be delivered. The IP10-AP fusions described herein may also be used when decreased aggregation is needed or desired to deliver a therapeutic dose.

The IP-10 ligand fusion polypeptide may be generated using standard techniques of molecular biology to generate fusions encoded from a suitable vector (Sambrook et al., *Molecular Cloning: A Laboratory Manual*, Cold Spring Harbor Laboratory Press, New York (1989)). The usefulness of such gene fusion constructs may be determined using the methods described above in the experimental methods and below in the examples, among others. The invention includes administering either type of fusion polypeptide alone or in a pharmaceutically acceptable carrier.

Thus, the formulations of this invention can be applied for example by parenteral administration, intravenous, subcutaneous, intramuscular, intracranial, intraorbital, opthalmic, intraventricular, intracapsular, intraspinal, intracisternal, intraperitoneal, intranasal, aerosol, or oral administration.

Therapeutic Formulations may be in the form of liquid solutions or suspensions; for oral administration, formulations may be in the form of tablets or capsules; and for intranasal formulations, in the form of powders, nasal drops, or aerosols.

Methods well known in the art for making formulations are to be found in, for example, "Remington's Pharmaceutical Sciences". Formulations for parenteral administration may, for example, contain excipients sterile water or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of present factors. Other potentially useful parenteral delivery systems for the factors include ethylene-vinyl acetate copolymer particals, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally.

VI. THERAPEUTIC ADMINISTRATION OF IP-10 IN A VIRAL VECTOR

The following example illustrates, but does not limit the invention.

Retroviral vectors, or other viral vectors such as adenoviral vectors with the appropriate tropisms for cells useful for therapeutic delivery, may be used as a gene transfer delivery system for the IL-10 polypeptide. Numerous vectors useful for this purpose are generally known have been described (Miller, Human Gene Therapy p. 15–14 (1990); Friedman, Science 244:1275–1281 (1989); Eglitis and Anderson, Bio-Techniques 6:608–614 (1988); Tolstoshev and Anderson, Current Opinion in Biotechnology 1:55–61 (1990); Sharp, The Lancet 337:1277–1278 (1991); Cornetta et al., Nucleic Acid Research and Molecular Biology 36:311–322 (1987); Anderson, Science 226:401–409 (1984); Moen, Blood Cells 17:407–416 (1991); and Miller and Rosman, Biotechniques 7:980–990 (1989)). Retroviral vectors are particularly well developed and have been used in a clinical setting (Rosenberg, et al. N. Engl. J. Med 323:370 (1990)).

The retroviral constructs, packaging cell lines and delivery systems which may be useful for this purpose include, but are not limited to, one, or a combination of, the following: Moloney murine leukemia viral vector types; self inactivating vectors; double copy vectors; selection marker vectors; and suicide mechanism vectors. The Moloney murine leukemia retroviral system of IP-10 delivery is particularly useful since it targets delivery of the IP-10 protein to the hematopoietic cells which may be used for autologous of non-antologous therapy.

Fragments or derivatives of the IP-10 polypeptide may also be administered by retroviral gene transfer therapy or another suitable viral vector system. Fragments or derivatives are defined as described above. Useful fragments or derivatives of IP-10 may be administered by inserting the nucleic acids encoding these fragments or derivatives in place of the complete IP-10 encoding gene in a gene therapy vector, as described above. Such constructs may be tested using the methods for testing the effects of IP-10 on viral infectivity described above, among others.

VII. NON VIRAL METHODS FOR THE THERAPEUTIC DELIVERY OF NUCLEIC ACID ENCODING IP-10

Nucleic acid encoding IP-10 or a fragment thereof, under the regulation of the appropriate promotor, and including the appropriate sequences required for insertion into genomic DNA of the patient, or autonomous replication, may be administered to the patient using the following gene transfer techniques: microinjection (Wolff et al., Science 247:1465 (1990)); calcium phosphate transfer (Graham and Van der Eb, Virology 52:456 (1973); Wigler et al., Cell 14:725 (1978); Felgner et al., Proc. Natl. Acad. Sci. USA 84:7413 (1987)); lipofection (Felgner et al., Proc. Natl. Acad. Sci. USA 84:7413 (1987); Ono et al., Neuroscience Lett 117:259

(1990); Brigham et al., Am. J. Med. Sci. 298:278 (1989); Staubinger and Papahadjopoulos, Meth. Enz. 101:512 (1983)); asialorosonucoid-polylysine conjugation (Wu and Wu, J. Biol. Chem. 263:141621 (1988); Wu et al., J. Biol. Chem. 264:16985 (1989)); biolistic transformation; and electroporation (Neumnn et al., EMBO J. 7:841 (1980)). These references are hereby incorporated by reference.

VIII. USE OF ALKALINE PHOSPHATASE FUSIONS TO PREVENT CHEMOKINE AGGREGATION

We have shown that fusions of alkaline phosphatase amino acid sequence to IP-10 prevent protein aggregation which otherwise interferes with the ability to detect receptor-ligand interactions. Despite the addition of the AP sequences, IP-10 retains its HSPG receptor binding capacity and the ability to inhibit endothelial cell proliferation. This technique (including the recombinant DNA methods provided herewith) may be used to make AP fusions which prevent the aggregation to other chemokines known to aggregate. For example, PF4, RANTES, and MIP-1β may be covalently linked to AP polypeptide sequences at either their carboxy or amino termini. It will be appreciated that while the whole chemokine sequence may be used, deletions on either end may also be introduced. The usefulness of a given fusion may be ascertained by assaying AP activity in a binding assay and using other known assays for the biological activity of the chemokine which is a part of the fusion. For example, chemotaxis of leukocytes and $Ca^{2+}$ flux (see below) may be measured.

IX. DETECTION OF COMPOUNDS WHICH BIND THE HSPG RECEPTOR

IP10-AP fusions, in combination with cells having an HSPG receptor, may be used to detect compounds which are capable of competing with IP-10 for the receptor binding site. It will be appreciated that such compounds may be used to enhance IP-10 modulated endothelial cell proliferation by preventing endogenous IP-10 from binding. Alternatively, compounds which compete may be useful as synthetic mimetics of IP-10 function. Compounds which either enhance or inhibit IP-10 function may also be used to modulate the effect of therapeutically administered IP-10.

To detect competitive binding one may use the assays provided below in the examples or one may use other assays known for assaying receptor-ligand binding and alkaline phosphatase activity.

Compounds which are determined to bind the HSPG receptor may be characterized for their ability to block or enhance IP-10 and/or PF4 biological activity using any number of assays provided here known in the art.

The following examples are provided to illustrate, but not to limit, the invention.

X. EXAMPLES

1. Experimental Procedures

Materials. Heparin was obtained from Hepar Inc., Franklin, Ohio Heparan sulfate, chondroitin sulfate A, chondroitin sulfate B, heparinase I, heparinase III (heparitinase I) were obtained from Sigma (Catalogue numbers H-7641, C-0914, C-2431, H-2519 and H-889, respectively).

Recombinant (r) human IL-8 was purchased from Genzyme, human rMIP-1a, MIP-1b, RANTES and MCP-1 may be purchased from PeproTech. Human rPF4 was supplied by Repligen.

Cell lines and Cell Culture. Cell lines were obtained from American Type Culture Collection with the following exceptions: the SV40-transformed murine endothelial cell line SVEC (O'Connell, K. A. and M. Edidin. 1990. Journal of Immunology 144: 521–525.) was obtained from Dr. A. Lichtman, Brigham and Women's Hospital, Boston, Mass.; and CHO K1, 803 and 677 were obtained from Dr. J. Esko, University of Alabama, Birmingham, Ala. The 803 and 677 cell lines are mutant CHO cells, defective in heparan sulfate (HS) synthesis, derived from CHO-K1 parental wild-type CHO cells (Esko, J. D. 1992. Adv Exp Med Biol 97–106). Mutant 803 produces 5%–10% residual HS and about one-half the normal level of chondroitin sulfate. Mutant 677 does not synthesize HS and overexpresses chondroitin sulfate by a factor of 3 so that the total amount of sulfated glycosaminoglycan is comparable in 677 and wild-type cells. Mutant 677 lacks both N-acetylglucosaminyltransferase and glucuronosyltranferase, enzymes required for the polymerization of heparan sulfate chains (Lidholt, K. et al., 1992. Proceedings of the National Academy of Sciences of the United States of America. 89: 2267–2271). Human peripheral blood leukocytes and leukocytes non-adherent to nylon wool were kindly provided by Dr. Robert Finberg, Dana Farber Cancer Institute, Boston, Mass. Leukocytes were grown in RPMI supplemented with 10% fetal bovine serum (FBS) (Sigma), fibroblast lines and SVEC cells were grown in DMEM (Sigma) supplemented with 10% enriched calf serum (Sigma), human umbilical cord vein endothelial cells (HUVEC's) (Clonetech) were grown in M199 (Gibco) supplemented with 10% heat-inactivated FBS and 5 ng/ml basic fibroblast growth factor (bFGF) (R&D Systems, Minneapolis, Minn.), and wild-type and mutant CHO cells were grown in Ham0s F12 medium (Gibco) supplemented with 10% FBS. All media was supplemented with 50 U/ml penicillin, 50 mg/ml streptomycin and 2 mM L-glutamine; in addition the murine leukocyte lines were supplemented with 57 mM 2-mercaptoethanol. All cells were maintained at 37° C. and 5% CO2. Bone marrow cells were harvested from the femurs of pathogen-free FVB female mice as described (Celada, A., et al. 1984. Journal of Experimental Medicine 160: 55–74) and maintained either in 30% L-cell conditioned medium (source of M-CSF) and 20% FBS for 2 weeks to obtain macrophages or 50% WEHI conditioned medium (source of IL-3) for 4 weeks to obtain mast cells (Razin, E. et al., 1984. Journal of Immunology 132: 1479–1486).

Protein expression and purification. Recombinant murine IP-10 (2) beginning with the putative mature N-terminal Ile (nucleotide 129) and terminating with the C-terminal Pro (nucleotide 359) and recombinant human IP-10 (Luster, A. D., et al. 1985. Nature 315: 672–676) beginning with the mature N-terminal Val (nucleotide 132) and terminating with the C-terminal Pro (nucleotide 363) were engineered by PCR using the murine IP-10 (Luster, A. D. and P. Leder. 1993. Journal of Experimental Medicine 178: 1057–1065) and human IP-10 (Luster, A.D., et al. 1985. Nature 315: 672–676) cDNAs as templates, respectively, into the Bam H1 site of the Qiaexpress vectors pQE12 and pQE8 (Qiagen Inc., Chatsworth, Calif.) and then transformed into the *E. coli* strain M15. Expression of IP-10 in pQE12 results in a fusion protein containing a six histidine carboxy-terminal tag and expression of IP-10 in PQE8 results in a fusion protein containing an amino-terminal six histidine tag. In addition, both vectors also result in the addition of Met-Arg-Gly-Ser at the amino terminus of the his-tagged proteins. rIP-10 was purified by sedimentation of inclusion bodies through sucrose, solubilization of the inclusion bodies in 4MP guanidine HCl, affinity chromatography on nickel agarose (Qiagen Inc., Chatsworth, Calif.), and reverse phase HPLC (Waters). HPLC was performed on a C18 Vydac column (2.2 cm I.D.) at a flow rate of 9.5 ml/min, monitoring absorbance at 214 and 277 nm. The column was eluted with a linear gradient of increasing acetonitrile concentration. The specific conditions were: 5% B for 5 min, 5%–50% B over 30 min, 50%–90% B over 15 min, and then 95% B for 15 min with B being 80% acetonitrile/0.054% trifluoroacetic acid and the remaining percentage being A which was 0.06% trifluoroacetic acid in water. For the studies reported herein, following HPLC purification and lyophilization, IP-10 was dissolved in PBS; however, subsequently it was found that IP-10 was more soluble and aggregated less when it was dissolved in water. The concentration of purified protein was determined with a Bradford assay (Bio-Rad Laboratories, Melville, N.Y.) with bovine serum albumin and bovine gamma globulin as standards.

Two eukaryotic expression systems were employed to express human IP-10: a murine Moloney virus LTR based vector (Luster, A. D. and P. Leder. 1993. Journal of Experimental Medicine 178: 1057–1065) transfected into J558L plasmacytoma cells and a dihydrofolate reductase resistance plasmid, pJOD-S (Barsoum, J. 1990. DNA and Cell Biology 9: 293–300), transfected into the double DHFR deletion mutant CHO line DG44 (Chasin, L. 1986. Somatic Cell Molecular Genetics 12: 555–666). The complete human IP-10 coding sequence, the 5' Pst1-Cla1 fragment (nucleotides 1-384) of the human IP-10 cDNA, was blunt-end ligated into the EcoRI site of a MoLTR-SV40 I/pA-expression vector that had been treated with the Klenow fragment of DNA polymerase.

Transfection of J558L plasmacytoma cells was performed by electroporation (Potter, H. et al. 1984. Proceedings of the National Academy of Sciences of the United States of America 81:7161–7165). 20 mg of linearized MoLTR-IP10 expression vector plasmid DNA and 1 mg of linearized neomycin resistance plasmid pSV7Neo, were used to transfect 5×106 cells. After 48 hrs in RPMI medium, cells were centrifuged and resuspended in selective media containing 0.8 mg/ml of G418 (as calculated for 100% antibiotic activity; Genticin, GIBCO) and plated in serial dilutions into 96 well plates to clone by limiting dilution. G418 resistant cells from single wells were expanded and a second round of cloning by limiting dilution in selective media was performed to ensure clonality. One clone, 4B6, expressing ~20 ng/ml IP-10, as determined by a solid phase ELISA (Luster, A. D. and P. Leder. 1993. Journal of Experimental Medicine 178: 1057–1065), was chosen as the source of secreted IP-10.

To try to obtain higher levels of IP-10 secretion, a second eukaryotic expression system utilizing a one step methotrexate selection was employed. For this purpose, the complete coding sequence of human IP-10 was engineered into the Sal I site of the mammalian expression vector pJOD-S by blunt-end ligation. 200 mg of the expression plasmid pJOD-IP10 linearized with Aat II and 200 mg of sonicated herring sperm DNA were electroporated into the DHFR-deficient CHO clone DG44 as described (Barsoum, J. 1990. DNA and Cell Biology 9: 293–300). A one step amplification with 0.5 mM methotrexate (Sigma) was performed in 10% dialyzed FBS and MEM-a lacking ribonucleotides and deoxyribonucleotides (Gibco). Individual clones were picked after 14 days of selection by ring isolation and expanded. 25 clones were initially assayed for the level of IP-10 expression by Northern blot and immunoblot using rabbit anti-IP10 antiserum. Clone 12D3G4 expressed ~10 ng/ml of IP-10 (as determined subsequently by ELISA) and was chosen as the source of secreted IP-10. Conditioned medium from transfected cells grown in serum free medium (Nutridoma, Boehringer Mannheim, for J558L and CHO-S-SFM, Gibco, for CHO cells) was collected and passed over a heparin Sepharose column (Pharmacia). Following step elutions with a NaCl gradient, an aliquot of each fraction was analyzed by SDS-PAGE and Western blotting using an affinity purified rabbit anti-IP10 antibody (Luster, A. D. and J. V. Ravetch. 1987. Journal of Experimental Medicine 166: 1084–1097). The fraction containing IP-10 immunoreactive material was then purified by reverse phase HPLC using the acetonitrile gradient previously described. HPLC fractions were then analyzed by SDS-PAGE on a 12.5% SDS-polyacrylamide gel using a Tris/Tricine buffer system (Schagger, H. and J. G. von. 1987. Analytical Biochemistry 166: 368–379) that has good resolution in the low molecular weight region, followed by either Coomassie staining or western blotting using rabbit anti-human IP-10 antisera (see below). IP-10 purified from J558L and CHO had the same appearance on SDS-PAGE.

Antibody Preparation. For immunizations, both human and murine IP-10 were purified from E. coli as described above, except that the eluate from the nickel-agarose chromatography column was separated on a denaturing SDS-polyacrylamide gel. The region of the gel containing IP-10 was cut out and emulsified with complete Freund's adjuvant for the primary immunization and with incomplete Freund's adjuvant for subsequent immunizations. Approximately 200 mg of the carboxy-terminal tagged protein (IP-10-(His)6) was injected subcutaneously into each of three, eight week old, female New Zealand white rabbits. The rabbits were boosted twice, at one month intervals, with 100 mg of the amino-terminal tagged protein ((His)6-IP-10) per rabbit to ensure the generation of antibodies recognizing the native N- and C- termini of IP-10. Ten days after the second boost, the three rabbits were bled and serum was isolated and a portion pooled for affinity purification. Affinity purification of antiserums was performed as described (Luster, A. D. and J. V. Ravetch. 1987. Journal of Experimental Medicine 166: 1084–1097) using the his-tagged rIP-10 coupled to CNBr-activated Sepharose beads (Pharmacia).

Radiolabeling rIP-10. IP-10 purified from E. coli was labeled with the 125I Bolton and Hunter reagent (Amersham) according to the manufacturers instructions and unincorporated 125I-Bolton and Hunter reagent was removed on a NAP-5 column (Pharmacia). The Bolton and Hunter reagent was chosen to radiolabel IP-10 because IP-10 contains no tyrosines amenable to chemical modification with 125I. Radiolabeled IP-10 (specific activity 154 ng/mCi) was also supplied by Dr. Garth Brown (NEN/Dupont) who radiolabeled PeproTech IP-10 by the Bolton and Hunter method and then purified it by reverse phase HPLC.

Production of IP-10-AP Fusion Protein. Human and murine IP-10 was expressed as a soluble fusion protein with the secreted form of placental alkaline phosphatase (AP) by engineering the human and mouse cDNAs for IP-10 into the APtag vector (Flanagan, J. G. and P. Leder. 1990. Cell 63:185–194). This was accomplished by PCR using the 50 primer CGCAAGCTTCGGGAGACATTCCTCAATTGC (SEQ ID NO: 1) and the 30 primer CGCGGATCCAG-GAGATCTTTTAGACATTTC (SEQ ID NO: 2) for human IP-10 and the 50 primer ACAGATCTAAGCGCTTCATC-CACCGCTGA (SEQ ID NO: 3) and the 30 primer GCGAGATCTAGGAGCCCTTTTAGACCTTTT (SEQ ID NO: 4) for murine IP-10 and the human and mouse IP-10 cDNA clones as templates, respectively. Following digestion of the human PCR product with Hind III and Bam HI and the mouse PCR product with Bgl II, they were ligated into the Hind III/Bgl II and Bgl II site of the APtag vector, respectively. This resulted in fusion proteins that contained the authentic signal sequences and entire mature proteins fused in frame with secreted alkaline phosphatase (SEAP) via the 4 amino acid linker Gly-Ser-Ser-Gly (SEQ ID NO: 7) for human IP-10 and Arg-Ser-Ser-Gly (SEQ ID NO: 8) for murine IP-10.

The IP-10-APtag plasmids linearized with Sal I were co-transfected with the selectable marker pSV7neo into NIH3T3 cells by the calcium phosphate method. After selection with 0.4 mg/ml G418 (Gibco) in 96-well plates (6.4 mm/well), approximately 100 individual clones were screened for secreted alkaline phosphatase activity. This assay was performed by heating 50 ml of the supernatant at 65° C. for 10 min to inactivate background cellular phosphatase activity and then measuring the A405 on a Vmax kinetic microplate reader (Molecular Devices) after incubating with 1M diethanolamine (pH 9.8), 0.5 mM $MgCl_2$, 10 mM L-homoarginine (a phosphatase inhibitor), and 12 mM p-nitrophenyl phosphate (Sigma), all prepared as a 2× stock solution (SEAP buffer). The highest expressing NIH-3T3 clones, 18.G5 for murine and 17.G2 for human IP-10-AP produced 1000 mOD/ml/min and 800 mOD/ml/min, respectively, were used for the experiments described in this paper. A control NIH-3T3 clone expressing unfused SEAP was produced by transfecting with plasmid pBC12/CMV/SEAP.

To determine the specific activity of the proteins, the concentration of IP10-AP in the supernatant was estimated by quantitative immunoprecipitation (see below) followed by SDS-PAGE with Coomassie blue staining and comparing the intensity of Coomassie staining compared to bovine serum albumin standard dilution. To determine the efficiency of immunoprecipitation, the amount of alkaline phosphatase activity in the initial sample and that remaining following two sequential immunoprecipitations was determined and used as a correction factor to calculate for less than 100% efficiency of immunoprecipitation. The resulting estimate for the specific activity of murine IP10-AP was 30 mOD/min/ng which is similar to the specific activity determined for IL4-AP (100 mOD/min/ng).

Immunoprecipitation and Immunoblotting. One ml of conditioned media from the NIH-3T3 clone 18.G5 secreting mIP10-AP was collected, centrifuged at 1000×g, and protease inhibitors (Boehringer Mannheim Biochemicals, Indianapolis, Ind.) were added to the supernatant at the following concentrations: Leupeptin (0.3 ng/ml), Aprotinin (10 ng/ml), PMSF (20 ng/ml) and pepstatin (0.8 ng/ml). The supernatant was then centrifuged at 10,000×g for 30 minutes at 4° C. and then precleared for 4 hrs at 4° C. with 50 ml of a 1:1 slurry of Protein A Sepharose (PAS)(Pharmacia). The PAS was then centrifuged at 10,000×g in eppendorf tubes, and 50 ml of a 1:1 slurry of a monoclonal antibody to placental alkaline phosphatase (Medix Biotech, catalog number A-018-02) coupled to CNBr-activated Sepharose (Pharmacia) was added to the supernatant for 2 hrs at 4° C. The beads were recovered by centrifugation at 10,000×g for 10 min. and a second immunoprecipitation was performed by adding another 50 ml of a 1:1 slurry of Mab-Sepharose beads and incubating for another 2 hrs at 4° C. The immunoprecipitates were then washed 3× with 1 ml of RIPA buffer (0.15M NaCl, 1% NP40, 0.1% SDS, 0.5% deoxycholate, 0.05M Tris, pH 8.0) and then boiled for 3 min in 50 ml of sample buffer containing 0.3M 2-ME, 4% SDS. 20 ml was then analyzed on a Laemelli 7% SDS-polyacrylamide gel and the intensity of Coomassie staining compared to a dilution series of bovine serum albumin.

For immunoblotting, gels were transferred to Immobilon-P membrane (Millipore, Bedford, Mass.) with a semidry transblotter (Owl Scientific, Woburn, Mass.) blocked with 3% Nonfat dry milk/3% goat serum (Sigma) /PBS and incubated with a 1:10,000 dilution of affinity purified rabbit anti-IP10 antiserum for 2 hrs at room temperature. The membranes were then washed 2×10 min each with PBS/0.1% Tween-20, 1×10 min with RIPA buffer and then 2×10 min each with PBS/0.1% Tween-20 and then incubated with a 1:20,000 dilution of peroxidase conjugated goat anti-rabbit IgG (Jackson ImmunoResearch Labs, West Grove, Pa., catalog #111-035-003) for 1 hr at room temperature in 3% nonfat milk and 3% goat serum in PBS. The membrane was then washed as described above and developed using an ECL chemiluminescence kit (Amersham).

Binding Assays. For non-adherent cells, $10^7$ cells were washed 1× with ice-cold binding buffer (HBSS/10 mM Hepes/0.1% ETSA) and resuspended in the indicated concentration of IP10-AP and competitors in a total of 100 ml ice-cold binding buffer. Binding was carried out for 2 hrs on ice with occasional mixing. Cells were washed 5× with ice cold binding buffer by repeated centrifugation at 4° C. Cell bound AP activity was determined by lysing cells in 100 ml 10 mM Tris (pH 8.0)/1% Triton X-100, heating at 65° C. for 10 min to inactivate cellular alkaline phosphatase, and then centrifuging at 14,000×g for 10 min. 50 ml of the soluble lysate was then mixed with 50 ml 2× SEAP buffer in a 96 well plate at room temperature and the colormetric product was assayed in a kinetic plate reader at A405. For adherent cells with higher numbers of binding sites, binding was determined in 6 well cluster plates. Cells were washed 2× with ice-cold binding buffer and incubated with the indicated concentration of IP10-AP and competitor in a total of 500 ml of ice-cold binding buffer for 2 hrs in the cold room on a rocker platform. Cells were washed 6× with binding buffer, lysed with 100 ml 10 mM Tris pH 8.0/1% Triton X-100, scraped into an eppendorf tube and then assayed as described above. Non-specific binding was determined in one of two ways. For the calculation of the equilibrium constant, non-specific binding was determined by adding 10 mM rIP-10 at each concentration of IP10-AP and performing the binding experiments in parallel exactly as described above. Specific binding was determined by subtracting background from total binding. Specific binding data was analyzed with the binding equation $B=(B_{max} \times F)/(K_d+F)$ (where B is bound ligand and F is free ligand) (28) using the program KaleidaGraph on a Macintosh computer. For other experiments non-specific binding was determined by adding equal amounts of nonfusion SEAP or cross-species IL4-AP (human IL4 does not bind to mouse cells and mouse IL4 does not bind to human cells) and performing the binding experiments in parallel exactly as described above. To obtain IP10-AP at concentrations higher than the concentration found in the conditioned medium of transfected cells, transfected cells were maintained in serum free DMEM for 14 days and the conditioned medium was concentrated 100-fold by ultrafiltration (Amicon, Beverly, Mass.). 125I-IP10 binding to cells was performed essentially as described above for IP10-AP binding except the cell pellet with bound IP-10 was counted in a gamma-counter.

Heparinase and Trypsin Treatment. For adherent cells, $10^6$ cells were washed 1× with serum-free DMEM and then incubated in 500 ml serum-free DMEM at 37° C. and 5%

CO2 for 1 hr with either 2.5 U/ml heparinase I or 0.2 U/ml heparinase III (heparitinase) (Bashkin, P. et al. 1989. Biochemistry 28: 1737–1743). For non-adherent cells, 107 cells were washed 1× with serum-free RPMI and resuspended in 100 ml RPMI plus the concentrations of Heparinase I and II indicated above. Following enzyme treatment adherent cells were washed 4× with 5 ml binding buffer and non-adherent cells were washed 2× with 10 mls binding buffer then assayed for IP10-AP binding as described above. Confluent monolayers (~107 cells) of adherent cells were washed 1× with calcium and magnesium free HBSS and incubated for 5 min 37° C. and 5% CO2 with 0.25% trypsin/0.02% EDTA (JRH Biosciences, Lexena, Kans.). Following enzyme treatment, the cells were washed with 10 mls DMEM/10% FBS and with 10 ml binding buffer and then resuspended in 100 ml binding buffer and assayed for IP10-AP binding as described above.

Endothelial Cell Proliferation Assay. Human umbilical vein endothelial cells (HUVECOs) were routinely used between passages 17–30. Cellular proliferation was determined by incorporation of [3H]-thymidine into DNA as previously described (Maione, T. E. et al. 1990. Science 247: 77–79). Briefly, rhIP-10 and rhPF4 were added to HUVECs plated in 9E6 well plates (6×103 cells/well) grown in M199/10% FBES/5 ng/ml FBS. Three days later the amount [3H]-thymidine incorporated into DNA per well was determined. Samples were tested in triplicate.

Calcium Flux. THP-1, A20 cells and EL4 cells were resuspended at 2×106 cells/ml in RPMI 1640 containing 2% FBS and 5 mg/ml Fura 2-am (Molecular Probes) (diluted from a 1 mg/ml stock in dimethyl sulfoxide). THP-1 cells were incubated for 1 hr and A20 and EL4 cells were incubated for 30 min at 37° C. and were then washed three times in 145 mM NaCl, 4 mM KCl, 1 mM NaH2PO4, 0.8 mM MgCl2, 1.8 mM CaCl2, 10 mM glucose, and 25 mM HEPES (pH 7.4). Cells were resuspended at 106 cells/ml in this buffer, and 2 ml samples were loaded into a Perkin-Elmer LS-5B fluorimeter for measurements of intracellular calcium. Excitation and emission wavelengths were 399 and 510 nm, respectively. Maximum and minimum calcium-Fura 2 fluorescences were measured using 1% Triton X-100, and 100 mM Tris (pH 8.0) plus 100 mM EGTA, respectively.

2. Purification of rIP-10

Purification of rIP-10 Expressed in *E. coli*.

Human and murine IP-10 were generated as recombinant (r) proteins tagged at either the N- or C- terminus with 6 histidines. Both N-terminally and C-terminally his-tagged IP-10 were generated to minimize the possibility that the 6 histidine tag could interfere with receptor binding and biological activity or mask a potentially important epitope when raising antibodies to rIP-10. IP-10 was purified by sedimentation of inclusion bodies (which contained the insoluble recombinant protein) through sucrose, solubilization of the inclusion bodies in 4M guanidine HCl, affinity chromatography on nickel agarose, the bound fraction was applied to a C-18 Vydac column and then reverse phase HPLC eluted with an acetonitrile gradient (FIG. 1A). Although there appears to be a shoulder on the IP-10 peak, SDS-PAGE analysis of fractions across this peak revealed a homogenous protein. IP-10 was then radiolabeled with 125I-Bolton and Hunter reagent and subjected to reducing SDS-PAGE (FIG. 1B). Under these purification conditions IP-10 appears to aggregate into multimers. At the exposure shown in FIG. 1B monomers and dimers are evident; but at longer exposures and on heavily loaded Coomassie stained gels higher order multimers are seen. These multimers are reactive with affinity purified rabbit anti-IP10 antiserum and are unaffected by reduction and irreversible alkylation of sulfhydryls. This aggregation is not the result of the 6 histidine tag, since a non-fusion version of IP-10 (Dupont/NEN) behaved similarly (FIG. 1B).

Purification of rIP-10 Secreted from J558L Plasmacytoma and CHO cells.

Since IP-10 purified from *E. coli* aggregated, it was of interest to determine if IP-10 purified from eukaryotic cells, and not subjected to denaturation and renaturation would also aggregate. The complete IP-10 cDNA was therefore engineered into the two expression vectors, MoLTR/SV40 I/pA and pJOD-S, and then stably transfected into J558L and CHO cells, respectively. IP-10 was secreted from both stably transfected lines in similar amounts as judged by a solid phase ELISA and had similar electrophoretic mobility profiles. IP-10 was purified from conditioned medium by heparin Sepharose affinity chromatography followed by reverse phase HPLC (FIGS. 2A–2C). This purification demonstrates that IP-10 binds to heparin Sepharose at physiological NaCl concentrations and is eluted between 0.5M and 1.0M NaCl (FIG. 2A). The 1M eluate from the heparin Sepharose column was subjected to reverse phase HPLC analysis (FIG. 2B). Fractions eluted with a gradient of increasing acetonitrile were analyzed by SDS-PAGE and immunoblotted with an affinity purified anti-IP-10 antiserum (FIG. 2C). The fraction containing immunoreactive IP-10 is indicated on the chromatogram in FIG. 2B by an arrow. IP-10 secreted and purified from eukaryotic cells also aggregates under these purification and electrophoresis conditions (FIGS. 2A, 2C). Therefore, the aggregation of the *E. coli* synthesized material is not unique to the bacterial product and reflects a property of the molecule. Furthermore, the *E. coli* and J558L produced IP-10 have the same reverse phase HPLC elution profile (compare position of curved arrow on chromatogram in FIG. 1a with position of curved arrow on chromatogram in FIG. 2b), suggesting they have similar properties.

3. IP10-AP Binding to Cells is Specific, Saturable and Competed by :PF4

Since radiolabeled rIP-10 produced in *E. coli* aggregated in solution and on cell surfaces (see below) it was impossible to identify a specific, saturable IP-10 binding site. To overcome this problem, IP-10 was expressed as an alkaline phosphase fusion gene that, when introduced into mammalian cells, resulted in the secretion of a non-aggregating monomeric fusion protein that bound to cells via its N-terminal IP-10 epitope and enzymatically assayed via its C-terminal alkaline phosphatase tail (FIGS. 3A and 3B). Both murine and human IP-10 were engineered into the APtag vector and initially used for binding studies. The APtag vector carries high level transcription control elements from the Moloney murine leukemia virus LTR, 30 splice and polyadenylation signals from the rat insulin gene and a domain of the human placental alkaline phosphatase gene. Inserting the murine IP-10 cDNA into the cloning site results in the creation of an IP10-alkaline phosphatase fusion gene (FIG. 3A).

Since no species specificity was apparent and the murine fusion protein had less nonspecific binding, all data presented in this report used the murine IP10-AP alkaline phosphatase fusion protein (IP10-AP). The specific activity of the IP10-AP was estimated by determining the amount of alkaline phosphatase activity in 1 ml of conditioned medium and then estimating the amount of IP10-AP protein by quantitative immunoprecipitation using a Mab specific for alkaline phosphatase.

Using IP10-AP, we have been able to demonstrate that IP-10 binds specifically to a variety of cells and binds with a Kd=25 nM on A20 B cells (FIG. 4A; 107 AZO B-cells were incubated with increasing concentrations of MIP10-AP and non-specific binding was determined by performing the biding assay at each concentration of IP10-AP in the presence of excess unlabelled marine IP-10. IP10-AP binding was 100% inhibited by 10 mM recombinant murine or human IP-10 on A20 B cells and EL4 T cells; however, when other chemokines were tested for their ability to compete for IP10-AP binding to A20 B cells and EL4 T cells, only hPF4 could inhibit 100% of mIP10-AP binding. At ~100 fold molar excess hIL-13, hMIP-1a, hMIP-1b and hRANTES had virtually no effect, but hMCP-1 did partially compete. Since hMCP-1 partially competed in one experiment, we performed a dose-inhibition experiment comparing mIP-10, hPF4 and hMCP-1 (FIG. 4B; 107 AZO B-cells were incubated with IS IP10-AP M murine in the presence of the indicated concentrations of unlabelled recombinant chemokines or heparin for two hours at 4° C. and cells were then washed and bound IP10-AP assayed). Non-specific binding was determined by the amount of human IL4-AP or secreted AP bound to murine AZO cells and was usually <1% of the total binding. In this experiment, while hPF4, mIP-10 and heparin (see below) could compete for IP10-AP binding to cells in a dose-dependent manner, hMCP-1 had no effect on mIP10-AP binding even at 100 mg/ml (~10 mM or ~600 fold molar excess). The discrepancy between the two experiments could relate to a change in the source of hMCP-1 (from Genentech to PeproTech). Of note, the inhibition curve using *E. coli* produced IP-10 was shifted to the right probably because the effective molarity of the IP-10 solution was lower than expected due to the aggregation of rIP-10.

4. IP10-AP Inhibits the Aggregation of IP-10 on Cells

To test the hypothesis that the alkaline phosphatase tail of the IP10-AP fusion protein was inhibiting the aggregation of IP-10 on the cell surface, A20 B cells were incubated for 2–4 hours at 4° C. with 125I-hIP10 (NEN/Dupont) in the presence of increasing concentrations 10 nM of either unlabeled hIP-10 or IP10-AP. The cells were then washed 5x with binding buffer and assayed for cell-bound 124I-hIP10. As can be seen in FIG. 5, the addition of cold competitor hIP-10 resulted in more 125I-hIP10 binding to cells, whereas the addition of IP10-AP was able to compete with 125I-hIP10 binding to intact cells. Thus, the increased binding of 125I-IP10 to cells in the presence of increasing cold non-fusion IP-10 is likely the a consequence of aggregation of IP-10 on the cell-surface.

5. IP-10 Binding Does Not Induce a Calcium Flux

Since most chemokines have been reported to induce a transient calcium flux in cells that have specific cell surface receptors, we tested the ability of IP-10 to flux calcium in A20 B cells and EL4 T cells. Neither the A20 or EL4 cell lines fluxed calcium in response to recombinant *E. coli* (or J558L) produced mIP-10 or to mIP10-AP even though the A20 B cell line fluxed calcium following cross-linking of its membrane bound IgG with an anti-IgG2b Mab. We also tested the responsiveness of the THP-1 cell line to IP-10 stimulation. THP-1 cells are a monocytic cell line that can specifically bind IP-10 (albeit at lower levels than the A20 or EL4 cell lines) and have been reported to flux calcium to various chemokines. The data shown in FIG. 6A demonstrates that the binding of mIP10-AP to THP-1 cells can be inhibited by excess human or mouse IP-10, but not hMIP1a or hMIP1b. In addition, HL60 cells do not bind mIP10-AP and were included as a negative control. As can be seen in FIG. 6B, THP-1 cells loaded with Fura-2 were able to demonstrate a transient calcium flux upon stimulation with hMCP-1, hRANTES and hMIP1a, but were unable to flux calcium upon addition of hIP-10. Furthermore, hIP-10 was unable to desensitize THP-1 cells to subsequent hMCP-1 or hRANTES stimulation. In contrast, hMIPP1a desensitized THP-1 cells to subsequent hRANTES or hMCP-1 stimulation. In addition, heparin and heparan sulfate (100 ng/ml), molecules that augment IL-8 signal transduction (Webb, L. M. et al. 1993. Proc Natl Acad Sci U.S.A. 90: 7158–7162), did not enable IP-10 to signal.

6. Glycosaminoglycan Inhibition of IP-10 Binding

Heparin and heparan sulfate were able to completely block IP10-AP binding to cells in a concentration-dependent manner (FIG. 7). Chondroitin sulfate B (dermatan sulfate) was also able to inhibit IP10-AP binding to A20 B cells, but at higher concentrations than heparin or heparan sulfate. In contrast, chondroitin sulfate A had no effect on IP10-AP binding even at 1 mg/ml—a concentration 100× that which gave complete inhibition by heparin and heparan sulfate. In fact, heparin's inhibition curve was almost superimposable on PF4's inhibition curve (FIG. 4B).

7. Cellular Distribution of IP-10 Binding Sites

Table 1 summarizes the results of multiple experiments showing the cellular distribution and approximate density of IP-10 binding sites on a number of different cell types. IP-10 binding sites are present in higher numbers on adherent cells like endothelial cells, fibroblasts and endothelial cells. Furthermore, IFN$_\gamma$ pretreatment of BM macrophages, U937, THP-1, or HL60 cells did not induce IP-10 binding sites on these cells. In addition, the activation of thymocytes with anti-CD3Mab (2C11) for 24 hrs had a minimal (~2 fold) enhancement of IP10 binding sites. As seen with other cells, however, IP-10 binding to resting or activated thymocytes was inhibited by heparin or heparan sulfate and binding was completely lost if the cells were treated with heparinase. Unfractionated human peripheral blood leukocytes had trace IP-10 binding that was lost if the cells were passed over nylon wool, indicating that binding sites are located on macrophages or B cells and not on peripheral blood T cells.

TABLE 1

EXPRESSION OF 1P-10 BINDING SITES BY DIFFERENT CELL TYPES

| Cell Type | Cell Line | ~Sites/cell | Nondetectable |
|---|---|---|---|
| Endothelial | SVEC | 400,000 | |
| Fibroblast | NIH/3T3 | 330,000 | |
| | Balbc/3T3 | 165,000 | |
| Endothelial | CHO K1 | 1,650 | CHO 833 and 677 |
| Monocytic | THP-1 | 1,320 | U937,J774, RAW 264.7 |
| B lymphocytic | A20, AJ9 | 660 | MIC, BJAB |
| T lymphocytic | EL4, LBRM | 330 | JURKAT, HSB, MBP |
| Leukocytes | Unfractionated | Trace | Nylon passed |
| BM culture | Macrophages | 825 | Mast cells |
| Thymocytes | Resting | 165 | |

Nondetectable indicates there was no significant binding over background binding. Background binding was determined using either cross-species IL4-AP or secreted AP binding to cells. Number of sites per cell was determined by using the specific activity estimated for IP10-AP (30 mOD/min per ng).

8. IP-10 Binding to Cells is Dependent on Surface Heparan Sulfate Proteoglycan (HSPG)

Since heparin and heparan sulfate inhibited IP10-AP binding to cells, and IP10-AP binding sites were found in higher numbers on adherent cell lines, we tested whether this binding site is salt and heparinase sensitive. FIG. 8A demonstrates that the IP10-AP binding site on fibroblasts is also competed for by heparin and excess IP-10 and sensitive to heparinase treatment and a 1M NaCl wash. Samples labeled Hase 1 were treated for 30 minutes at 37° C. with heparinase 1 in serum free medium and then washed with complete medium prior to the binding assay. Following binding, all cells were washed 5× in HBSS; the samples labeled 1M NaCl received an additional 1 min wash with HBSS adjusted to 1M NaCl. The amount of bound alkaline phosphatase activity was then enzymatically determined. Heparinase I treatment of Balb/c 3T3 cells enzymatically removed ~75% of the IP10-AP binding site while having no effect on kit-AP binding to the kit ligand. Heparinase III also removed ~84% of the IP10-AP binding sites on NIH 3T3 cells. This is also true for the binding site on A20 B cells where Heparinase I and III removed 100% and 75%, respectively. In addition, following binding and washing in HBSS, a 1 min wash in HBSS adjusted to 1M NaCl removed all of the IP10-AP from Balb/c-3T3 and only 50% of Kit-AP from these same cells.

The IP-10 binding site is also sensitive to trypsin digestion on three cell lines tested, NIH-3T3, Balb/c-3T3 and SVEC—a mouse endothelial cell line (FIG. 8B). A further demonstration that IP-10 binding is dependent on cell surface heparan sulfate comes from studies using two CHO mutants that lack HSPG due to mutations in enzymes necessary for glycosaminoglycan biosynthesis. 106 cells were incubated for 2 hrs at 4° C. with 15 nM IP10-AP in the presence of 10 mM unlabeled mIP10 or the indicated concentration of heparin. The monolayers were then washed 5× with HBSS binding buffer and the amount of bound IP10-AP was determined. As can be seen in FIG. 9, IP10-AP binds to wild-type parental CHO line K1, but does not bind to either mutant lines, 677 and 803. In addition, soluble heparan sulfate does not restore binding to the mutants, but in fact inhibits the binding of IP10-AP to the wild-type CHO cells in a concentration dependent fashion.

9. IP-10 Inhibits Human Umbilical Cord Vein Endothelial Cell (HUVEC) Proliferation Since PF4 was able to compete with IP-10 for binding to several cell lines tested including A20 B cells and NIH 3T3 cells, and since PF4 was known to inhibit bFGF induced proliferation of endothelial cells, the effect of IP-10 on the growth of HUVECs was tested (FIG. 10A). Like PF4, which has an IC50 of 100–200 nM, IP-10 half maximally inhibits HUVEC proliferation at 150 nM (1.5 mg/ml). However, it required at least 5× more IP-10 to reach 100% inhibition compared to PF4, which again may reflect a propensity of IP-10 to aggregate at high concentrations decreasing its effective molarity. The inhibition by submaximal concentrations of PF4 and IP-10 are additive. As is the case for PF4, increasing concentrations of exogenous heparin reverses the inhibitory effects of IP-10 upon proliferation, just as it does the inhibitory effects of PF4 (FIG. 10B). A comparison of the binding affinity of each, IP-10 and PF4, for soluble heparin shows the Kd values to be equivalent at 10-7M. Neutralizing antibodies to PF4 that block PF4's inhibition of HUVEC proliferation had no effect on IP-10's inhibition of proliferation.

PF4 and IP-10 do not induce apoptosis in HUVECs; they cause a growth arrest. When PF4 or IP-10 are washed away (by the addition of heparin 5 U/ml) from HUVECs growth arrested by these chemokines, and fresh media containing bFGF is added back to the cultures, cellular proliferation resumes.

Other Embodiments

In other embodiments, the invention includes any protein which is substantially homologous to an IP-10 polypeptide (FIG. 11, SEQ ID NOS:5 and 6); such homologs include other substantially pure naturally occurring mammalian IP-10 proteins as well as allelic variations; natural mutants; induced mutants; proteins encoded by DNA that hybridizes to the IP-10 sequences of FIGS. 2 and 7 under high stringency conditions or low stringency conditions (e.g., washing at 2× SSC at 40° C. with a probe length of at least 40 nucleotides); and polypeptides or proteins specifically bound by antisera directed to a IP-10 polypeptide, especially by antisera to the active site or to the Max binding domain of an IP-10 protein. The term also includes chimeric polypeptides that include an IP-10 fragment.

The invention further includes analogs of any naturally occurring IP-10 polypeptide. Analogs can differ from the naturally occurring IP-10 protein by amino acid sequence differences, by post-translational modifications, or by both. Analogs of the invention will generally exhibit at least 70%, more preferably 80%, even more preferably 90%, and most preferably 95% or even 99%, homology with all or part of a naturally occurring IP-10 sequence. The length of comparison sequences will be at least 8 amino acid residues, preferably at least 24 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally occurring IP-10 polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, hereby incorporated by reference; or Ausubel et al., supra, hereby incorporated by reference). Also included are cyclized peptides molecules and analogs which contain residues other than L-amino acids, e.g., D-amino acids or non-naturally occurring or synthetic amino acids, e.g., β or γ amino acids.

In addition to full-length polypeptides, the invention also includes IP-10 polypeptide fragments. As used herein, the term "fragment" means at least 10 contiguous amino acids, preferably at least 30 contiguous amino acids, more preferably at least 50 contiguous amino acids, and most preferably at least 60 to 80 or more contiguous amino acids. Fragments of IP-10 can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which exhibit biological activity (for example, the ability to interfere with mammalian cell division as assayed herein). Preferably, an IP-10 polypeptide, fragment, or analog exhibits at least 10%, more preferably 30%, and most preferably, 70% or more of the biological activity of a full length naturally occurring IP-10 polypeptide.

Other embodiments are within the following claims.

What is claimed is:

1. A method of inhibiting non-neoplastic endothelial cell proliferation in a mammal having a pathological condition involving non-neoplastic endothelial cell proliferation, said method comprising administering to said mammal an IP-10 polypeptide, said administering in an amount sufficient to decrease non-neoplastic endothelial cell proliferation.

2. The method of claim 1, wherein said endothelial cell is a vascular endothelial cell.

3. A method of treating atherosclerosis in a mammal, said method comprising administering to said mammal an IP-10 polypeptide in an amount sufficient to decrease non-neoplastic endothelial proliferation associated with said atherosclerosis.

4. The method of claim 1 wherein said polypeptide is in a pharmaceutically acceptable carrier.

5. The method of claim 1 wherein said administering is by localized injection.

6. The method of claim 1 wherein said administering is by continuous release.

7. A method of inhibiting FGF-induced non-neoplastic endothelial cell proliferation in a mammal having a pathological condition involving non-neoplastic endothelial cell proliferation, said method comprising administering a therapeutically effective amount of IP-10 polypeptide.

8. The method of claim 1 or 7, wherein said mammal has a hemangioma.

9. A method of treating a keloid in a mammal, said method comprising administering to said mammal an IP-10 polypeptide in an amount sufficient to decrease FGF-induced, non-neoplastic endothelial proliferation associated with said keloid.

10. A method of treating a proliferative retinal disorder in a mammal, said method comprising administering to said mammal an IP-10 polypeptide in an amount sufficient to decrease FGF-induced, non-neoplastic endothelial proliferation associated with said proliferative retinal disorder.

11. A method of inhibiting TGFβ-induced non-neoplastic endothelial cell proliferation in a mammal having a pathological condition involving non-neoplastic endothelial cell proliferation, said method comprising administering a therapeutically effective amount of IP-10 polypeptide.

12. A method of treating inflammation in a mammal, said method comprising administering to said mammal an IP-10 polypeptide in an amount sufficient to decrease TGFβ-induced, non-neoplastic endothelial proliferation associated with said inflammation.

13. A method of treating fibrosis in a mammal, said method comprising administering to said mammal an IP-10 polypeptide in an amount sufficient to decrease TGFβ-induced, non-neoplastic endothelial proliferation associated with said fibrosis.

* * * * *

UNITED STATES PATENT AND TRADEMARK OFFICE
CERTIFICATE OF CORRECTION

PATENT NO. 5,824,299
DATED      October 20,1998
INVENTORS  Andrew Luster and Philip Leder It is certified that error appears in the above-identified patent and that said Letters Patent is hereby corrected as shown below:

Col. 3, line 44, replace "encoding an the polypeptide" with --encoding the polypeptide--;

Col. 10, line 17, replace "Charges in the degree of" with --Changes in the degree of--;

Col. 7, lines 44-45, replace "(Seq. ID No.5) and nucleic acid (Seq. ID No. 6) sequences" with --(Seq. ID NO. 6) and nucleic acid (Seq. ID NO. 5) sequences--;

Col. 11, line 32, replace "fused to the a ligand" with --fused to the ligand--;

Col. 15, line 1, replace "4MP guanidine" with --4M guanidine--;

Col. 18, line 22, replace "Hepes/0.1% ETSA" with --Hepes/0.1% BSA--;

Col. 19, line 24, replace "9E6" with --96--;

Col. 19, line 25, replace "M199/10% FBES" with --M199/10% FBS--;

Col. 21, line 8, replace "biding assay" with --binding assay--;

Col. 21, line 15, replace "hIL-13" with --hIL-8--;

UNITED STATES PATENT AND TRADEMARK OFFICE
CERTIFICATE OF CORRECTION

PATENT NO. : 5,824,299
DATED : October 20, 1998
INVENTORS : Andrew Luster and Philip Leder It is certified that error appears in the above-identified patent and that said Letters Patent is hereby corrected as shown below:

Col. 21, line 49, replace "IP-10 is likely the a consequence" with --IP-10 is likely a consequence--;

Col. 24, line 3, replace "(Fig. 11, SEQ ID NOS:5 and 6)" with --(FIG. 11, SEQ ID NO:6)--.

Signed and Sealed this

Twelfth Day of December, 2000

Attest:

Q. TODD DICKINSON

*Attesting Officer*       *Director of Patents and Trademarks*